United States Patent [19]
Huff et al.

[11] Patent Number: 5,998,593
[45] Date of Patent: Dec. 7, 1999

[54] FLUORESCENT ENZYME SUBSTRATES

[75] Inventors: Jeffrey B. Huff, Park Ridge; Barbara T. Merchant, Wilmette; Carolyn R. Mullen, Libertyville; Seshagiri R. Tata Venkata, Chicago, all of Ill.

[73] Assignee: Abbott Laboratories, Abbott Park, Ill.

[21] Appl. No.: 09/041,192

[22] Filed: Mar. 10, 1998

[51] Int. Cl.$^6$ ............... C07H 17/04; C07D 311/02
[52] U.S. Cl. ............... 536/4.1; 549/214; 549/283
[58] Field of Search ............... 536/4.1; 549/214, 549/283

[56] References Cited

U.S. PATENT DOCUMENTS

| | | | |
|---|---|---|---|
| 4,226,978 | 10/1980 | Boguslaski et al. | 536/4 |
| 5,208,350 | 5/1993 | Bouma et al. | 549/289 |
| 5,247,099 | 9/1993 | Celebuski | 549/289 |
| 5,272,260 | 12/1993 | Pope et al. | 536/18.1 |
| 5,342,970 | 8/1994 | Chalom et al. | 549/288 |
| 5,399,560 | 3/1995 | Cerami et al. | 514/242 |

FOREIGN PATENT DOCUMENTS

| | | |
|---|---|---|
| 2319250 | 5/1998 | United Kingdom . |

OTHER PUBLICATIONS

Adamczyk, M., et al., "Synthesis of 7–Hydroxy–4–(ω–Carboxyalkyl)coumarins and 7–(Dimethylamino)–4–(ω–Carboxyalkyl)Courmarins", *OPPI Briefs*, 28(5):627–633 (1996).

Baggett, N., et al., "7–Hydroxycoumarin–4–acethydrazide: A fluorescent derivatizing reagent for aldehydes and ketones", *Analytica Chimica Acta*, 265:111–115 (1992).

Baggett, N., et al., "7–β–D–Galactopyranosyloxy coumarin–4–acetic acid and its methyl ester as substrates for the β–D–galactosidase of *Escherichia coli*", *Carbohydrate Research*, 197:295–301 (1990).

Baker, W., et al., "Fluorescent Reagents. Acyl Chlorides and Acyl Hydrazides", *The University of Bristol*, 170–173 (1949).

Gayo, L., M., et al., "Use of Pentafluorophenyl Esters for One–Pot Protection/Activation of Amino and Thiol Carboxylic Acids", *Pergamon*, 4915–4918 (1996).

*Primary Examiner*—Amelia Owens
*Attorney, Agent, or Firm*—Paul D. Yasger

[57] ABSTRACT

Fluorescent enzyme substrates are provided. The substrates are derivatives of coumarin having an enzyme cleavable group at position 7 and a hydrophilic amide group at position 4. The compounds are highly water soluble, stable at ambient and reduced temperatures and fluoresce upon cleavage by an enzyme.

11 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 30 bases
        (B) TYPE: nucleic acid
        (C) STRANDEDNESS: double
        (D) TOPOLOGY: linear (ii) MOLECULE TYPE: synthetic DNA (xi) SEQUENCE DESCRIPTION: SEQ ID NO:1:

TTGTTTGAAC CGCATCTGAG CTTTTTTATC        30

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:2:

CCTGCACTGT ACCCCCAAT CC        22

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:3:

```
ATTCCCTACA ATCCCCAAAG TCAAGGAGT                                    29
```

(2) INFORMATION FOR SEQ ID NO: 4:

(i) SEQUENCE CHARACTERISTICS:
        (A) LENGTH: 170
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 4:

```
ATTCCCTACA ATCCCCAAAG TCAAGGAGTA ATAGAATCTA TGAATAAAGA             50

ATTAAAGAAA ATTATAGGAC AGGTAAGAGA TCAGGCTGAA CATCTTAAGA            100

GAGCAGTACA AATGGCAGTA TTCATCCACA ATTTTAAAAG AAAAGGGGGG            150

ATTGGGGGT ACAGTGCAGG                                              170
```

(2) INFORMATION FOR SEQ ID NO:5:

(i) SEQUENCE CHARACTERISTICS:
        (A) LENGTH: 163 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:5:

```
ATTCCCTACA ATCCCCAAAG TCAAGGAGTA ATAGAATCTA TGAATAAAGA             50

ATTAAAGAAA ATTATAGGAC AGGTAAGAGA TCAGGCTGAA CATCTTCTCA            100

AGCTCAGTAG TATATCATCC ACAATTTTAA AAGAAAAGGG GGGATTGGGG            150

GGTACAGTGC AGG                                                    163
```

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:6:

```
TCTCAAGCTC AGTAG                                                   15
```

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:7:

ACAGCAGTAC AAATGGCA                                                    18

FLUORESCENT ENZYME SUBSTRATES

TECHNICAL FIELD OF THE INVENTION

The present invention relates to enzyme substrates, and more particularly, the invention relates to coumarin derivatives that can be used as fluorescent enzyme substrates.

BACKGROUND OF THE INVENTION

Enzymatic substrates that become fluorescent after being acted upon by an enzyme generally are well known. Such fluorescent substrates typically have two components that are bound to one another through, for example, a covalent chemical bond. One component is a fluorescent molecule that is capable of fluorescing by first accepting light energy and then emitting light energy. The other component is an entity that prevents the fluorescent molecule from accepting or emitting light energy when the two components are covalently bound to one another. In the presence of an appropriate enzyme, the enzyme cleaves the covalent bond between the two components and separates one component from the other to permit the fluorescent molecule to accept and emit light energy. In other words, the enzyme frees the fluorescent molecule and allows it to fluoresce.

Fluorescent enzyme substrates, such as those described above, have demonstrated utility in the diagnostic industry. For example, fluorescent substrates have been used in diagnostic assays designed to detect disease causing agents such as an HIV analyte in a test sample. Heterogeneous immunoassays are one type of diagnostic assay where fluorescent substrates have been employed. According to such assays, an analyte which may be found in a test sample is separated from the test sample using a solid support material that is capable of specifically binding the analyte. The bound analyte can then be contacted with a conjugate comprising a specific binding member and an appropriate enzyme. The conjugate also specifically binds the analyte and a result, binds the enzyme to the analyte. The support material and any bound enzyme can then be contacted with a fluorescent enzyme substrate that can be cleaved by the enzyme. The enzyme acts upon the substrate to yield the fluorescent product that then can be detected as an indication of the presence of the analyte on the support material, and therefore in the test sample. Many other assay configurations using fluorescent enzyme substrates are well known.

Detecting fluorescence emitted from the fluorescent component of a fluorescent enzyme substrate is typically achieved in two steps. In particular, the fluorescent molecule is first excited with light energy and subsequently, the fluorescence emitted from the fluorescent component is then detected. Generally, fluorescent molecules can be excited with light energy from, for example, a laser or another suitable light source. Fluorescence is detected with a device designed to detect light energy of a wavelength that is emitted by the fluorescent molecule. Such excitation and emission detection systems generally are designed to operate at particular wavelength ranges and can be one of the most expensive components of an assay system.

Many fluorescent substrates and the enzymes that cleave these substrates to release fluorescent molecules are known. Ideally, fluorescent substrates should be soluble and stable in aqueous buffers, should have a high affinity for the enzymes that act upon them, and should yield a strong signal upon enzymatic action. Additionally, it would be advantageous to have a enzymatic substrate with all these properties and have spectral properties that are similar to presently existing fluorescent substrates. The advantage of having such a substrate resides in the fact that such a substrate would enable multiple analytes to be detected in a single assay without the need for additional excitation and detection systems to excite and detect a fluorescent molecule having distinct spectral properties.

Unfortunately, while many fluorescent substrates are known, substrates having all of the properties listed above are are currently believed to be unknown. For example, some substrates may have the desired spectral properties, but may not be sufficiently soluble. Other substrates may be sufficiently soluble but have stability problems such that the original compound breaks down in solution to yield an entirely different compound which may or may not have the spectral properties of the original compound. Still other substrates may not bind well with enzymes which thereby necessitates the use of excess substrate to yield a sufficiently detectable signal. Accordingly, there is a need for a fluorescent enzyme substrate that (i) is soluble and stable in aqueous buffers, (ii) has a high affinity for the enzymes that act upon it, and (iii) yields a strong signal upon enzymatic action. Moreover, there is a need for a fluorescent substrate that exhibits these properties and has spectral properties that are similar to existing substrates.

SUMMARY OF THE INVENTION

In one aspect, the present invention provides a fluorescent enzyme substrate having the formula (I), below

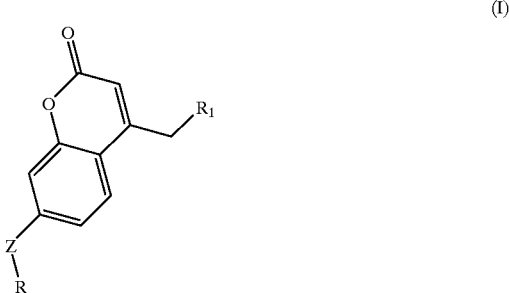

(I)

wherein R is an enzyme cleavable group; Z is O, S or Se; and $R^1$ is an amide. The enzyme cleavable group, R, typically is a monosaccharide, or a group having the structure —CO(CH$_2$)$_a$CH$_3$, or —PX(OR$^2$)$_2$ where $R^2$ is hydrogen or lower alkyl, X is O or S, and a is 1 to 18. Preferably, R is β-D-galactose. Of course, those skilled in the art will recognize that when R is —PX(OR$^2$)$_2$ and $R^2$ is hydrogen, the substrate (I) may exist as, for example Li$^+$, K$^+$ or Na$^+$ salts.

The substituent $R^1$ can be a chain of atoms attached to the rest of the substrate (I) with an amide linkage. The chain of atoms attached to the substrate (I) through the amide linkage is a branched or unbranched chain of 2–25 carbon atoms that terminates with a chemical group selected from one of following groups: —OH, —NH$_2$, —OC$_1$—C$_2$ alkyl, —COOH, —N(C$_1$—C$_2$ alkyl)$_2$, —SO$^-$$_3$, a heterocycle of 5–6 atoms that contains at least one N atom, and —N(C$_1$—C$_5$ alkyl amine)$_2$. In the event such a chain of atoms is branched, preferably all branches terminate with any of the above terminating groups. Additionally, the 2–25 carbon atom chain can optionally be substituted with one or more heteroatoms (e.g. O, N, or S) in addition to the heteroatoms found in the terminating groups mentioned above. Preferably, R1 is a group selected from —CONH(CH$_2$)$_2$OH, —CONHC(CH$_2$OH)$_3$, —CONH(CH$_2$)$_2$NH(CH$_2$)$_2$NH$_2$, —CONH(CH$_2$)$_2$N[(CH$_2$)$_2$NH$_2$]$_2$, —CONH[(CH$_2$)$_2$O]$_2$(CH$_2$)$_2$OCH$_3$, —CONH(CH$_2$)$_2$OCH$_3$, —CONH(CH$_2$)$_2$SO$_3$, —CONH(CH$_2$)$_2$COOH, or —CONH(CH$_2$)$_2$N(CH$_3$)$_3$.

The substrates herein provided can be used in any assay where substrate cleavage by an enzyme is used to generate a detectable fluorescent signal. In particular, compounds of the formula (I) can be employed to determine if a particular enzyme is present in a test sample whether or not the enzyme is an analyte or attached to an analyte through, for example a specific binding interaction. Hence, the substrate can be used in a variety of assay techniques including homogeneous, heterogeneous, competitive or sandwich assays.

For example, according to one method, the presence of an enzyme in a test sample can be detected by (a) contacting the test sample with the fluorescent enzyme substrate of having the formula (I); and (b) detecting fluorescence as an indication of the presence of the enzyme in the test sample.

According to another method an analyte in a test sample can be detected by (a) forming capture reagent/first analyte/first conjugate complexes by contacting the test sample with a first capture reagent and a first conjugate; (b) contacting the complex with the enzyme substrate of the formula (I); and (c) detecting a first fluorescent signal as an indication of the presence of the analyte in the test sample. Those skilled in the art will recognize that the enzyme substrate (I) also can be employed with additional reagents to detect multiple analytes in a test sample.

In another aspect, a kit is provided and comprises an enzyme substrate (I) in a suitable container. Depending upon the purpose of the kit, a kit according to the invention can further include an additional container or additional containers that contain, for example, a conjugate, a capture reagent, nucleic acid primers or probes, wash buffers, inactivating agents, control reagents and other reagents suitable for running an assay of interest.

Also provided are fluorescent compounds (II) below

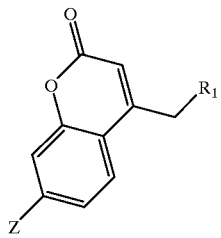

(II)

wherein $R^1$ and Z are defined as above.

DETAILED DESCRIPTION OF THE INVENTION

The present invention provides compounds that are useful as fluorescent enzyme substrates. It has been discovered that the $R^1$ group on the enzyme substrate (I) is very important in terms of the solubility, and stability of such fluorescent enzyme substrates. Moreover, the choice of the $R^1$ group has an impact on the affinity an enzyme has for such substrates. For example, fluorescent enzyme substrates having the structure (I) are very soluble. Additionally, once the substrates are in solution they are storage stable and therefore maintain structural integrity. Also, enzyme substrates having the structure (I) possess desirable spectral properties after enzymatic action. Moreover, the substrates provided herein have a high affinity for enzymes and therefore, the substrates are converted to fluorescent derivatives in an efficient manner. Hence, the substrates can be employed at reduced concentrations.

The fluorescent enzyme substrates of the present invention are represented by Structure (I), below

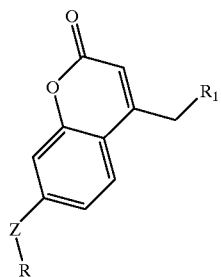

(I)

wherein R is an enzyme cleavable group; Z is O, S or Se; and $R^1$ is an amide. As used herein, the term "amide" means amides having the structure —CON— and is intended to include primary and secondary amides.

According to the present invention, enzymes act on the fluorescent enzyme substrates (I) such that they cleave the group designated R to thereby yield a detectable fluorescent product or molecule having the formula (II) and described further below. As used herein, the phrase "enzyme cleavable group" means a chemical group that can be cleaved or dissociated from the fluorescent enzyme substrate by virtue of enzymatic action. Enzymes and the groups that they can cleave from substrates are well known and a matter of choice for one skilled in the art. For example, enzymes that cleave sugar groups such as glycosaccharidases, galactosidases, and the like; dealkylases; phosphatases; phosphodiesterases; lipases; peroxidases; and esterases are enzymes that could be employed according to the present invention. Sugar cleaving enzymes and phosphatases are preferred enzymes and galactosidase and alkaline phosphatase, which cleave galactose and phosphate groups, respectively are more preferred.

Preferably, the enzyme cleavable group R is a monosaccharide; —CO(CH$_2$)$_a$CH$_3$; or —PX(OR$^2$)$_2$; where $R^2$ is hydrogen or lower alkyl, X is O or S, and a is 1 to 18. More preferably, R is a monosaccharide and selected from the group consisting of glucose, galactose, allose, altrose, mannose, and talose and most preferably, R is β-D-galactose.

$R^1$ can be a chain of atoms attached or bonded to the substrate (I) with an amide linkage. This chain can be a branched or unbranched chain of 2–25 carbon atoms that terminates with a chemical group selected from one of the following: —OH, —NH$_2$, —OC$_1$—C$_2$ alkyl, —COOH, —N(CO—C$_2$ alkyl)$_2$, —SO$_3$, a heterocycle of 5–6 atoms that contains at least one N atom, and —N(C$_1$—C$_5$ alkyl amine)$_2$. In addition, in cases where $R^1$ has side chains (or is branched), the side chains preferably also terminate with one of the above groups. Further, the branched or unbranched chain of 2–25 carbon atoms optionally can be substituted with one or more heteroatoms.

Preferably, $R^1$ is COR$^3$, wherein $R^3$ is NHY, and Y is —(CH$_2$)$_1$R$^5$ and R$_5$ is —CH$_2$OH; —COOH; —OCH$_3$; —OH; —[O(CH$_2$)$_m$]$_n$CH$_2$OH; —[O(CH$_2$)$_m$]$_n$OCH$_3$; —C[(CH$_2$)$_m$OH]$_3$; a heterocycle of 5 or 6 atoms that contains at least one N atom; —SO$^-$$_3$; —NH$_2$; —N$^+$[(CH$_2$)$_m$CH$_3$]$_3$. As a further alternative, Y can be —CH(R$^6$)(R$_7$); —(CHOHCONH)$_m$CHOHCOOH; —(CH$_2$CONH)$_m$CH$_2$COOH where R$^6$ is —CH$_2$OH or —COOH and R$^7$ is —CH$_2$OH or —(CH$_2$)$_p$NH$_2$ and where 1, m, n, and p, referenced above, are independently 1 to 6. Preferably, 1 is 1–3, m is 2 or 3, n is 2–3, and p is 1 to 6.

More preferably, $R^1$ is $COR^3$, $R^3$ is NHY, and Y is one of the following groups: —$(CH_2)_2OH$, —$C(CH_2OH)_3$, —$(CH_2)_2NH(CH_2)_2NH_2$, —$(CH_2)_2N[(CH_2)_2NH_2]_2$, —$[(CH_2)_2O]_2(CH_2)_2OCH_3$, —$(CH_2)_2OCH_3$, —$(CH_2)_2SO^-_3$, —$(CH_2)_2COOH$, and —$(CH_2)_2N^+(CH_3)_3$.

More preferably, $R^1$ is selected from one of the following groups: —$CONH(CH_2)_2OH$, —$CONHC(CH_2OH)_3$, —$CONH(CH_2)_2NH(CH_2)_2NH_2$, —$CONH(CH_2)_2N[(CH_2)_2NH_2]_2$, —$CONH[(CH_2)_2O]_2(CH_2)_2OCH_3$, —$CONH(CH_2)_2OCH_3$, —$CONH(CH_2)_2SO^-_3$, —$CONH(CH_2)_2COOH$, and —$CONH(CH)_2N^+(CH_3)_3$.

Most preferably, Z is O, R is β-D-galactose and $R^1$ is —$CONH(CH_2)_2OH$.

As used herein "heterocycle" shall mean a ring structure containing at least one non-carbon atom in the ring, which non-carbon atom is a hetero atom well known to those skilled in the art such as, for example, S, N, or O.

Substrates of the present invention can be synthesized using commercially available starting materials and general amide synthesis procedures known in the art such as, for example, procedures described in March, J., *Advanced Organic Chemistry*, Wiley Interscience, 420–423 (1992) and references cited therein. The exact synthetic procedures used depend, as is known in the art, on the nature of the enzyme cleavable group and the hydrophilic $R^1$ group.

Generically, the procedure for synthesizing enzyme substrates of the present invention begins with adding an enzyme cleavable group to the 7 position of 7-Hydroxycoumarin-4-acetic acid. The carboxylic acid moiety at the 4 position can then be converted to the corresponding amide via the in situ conversion of the carboxylic acid activate ester, followed by acylation of the activated ester by the corresponding amine. While other synthetic reoutes are possible (as shown in the examples), an exemplary synthetic scheme for producing such a compound is set forth below in Scheme 1.

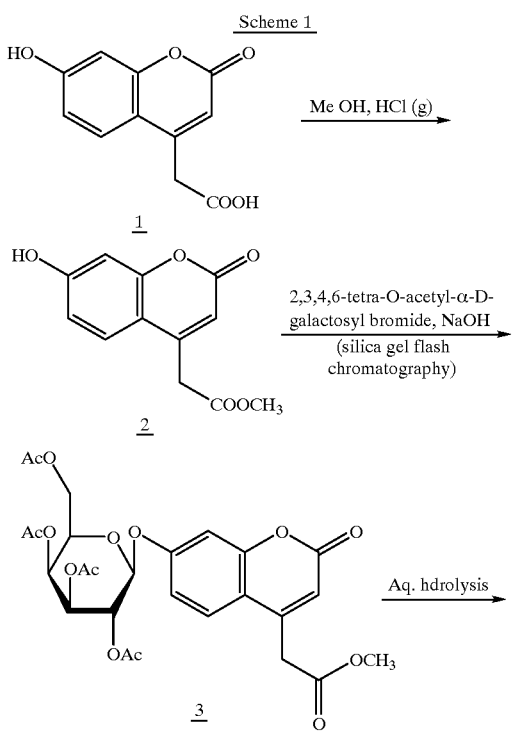

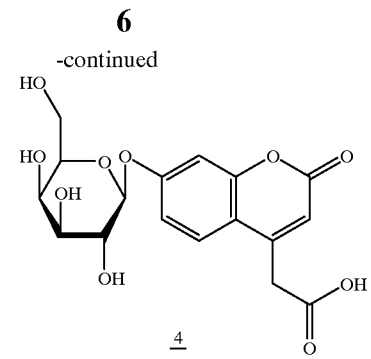

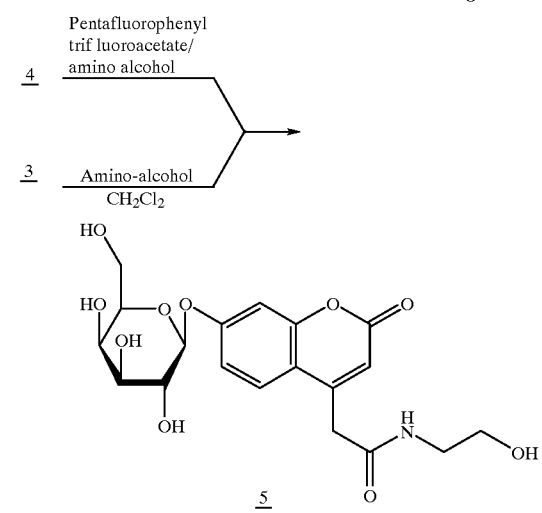

In accordance with exemplary Scheme 1, the carboxy function of 7-Hydroxycoumarin-4-acetic acid 1 (available from Aldrich Chemical Co., Milwaukee, Wis.) is protected by, for example, conversion to the methyl ester 2 via the Fischer Spier reaction using a procedure described by Baker, W., Haksar, C. N., McOmie, J. F. W., *J. Chem. Soc.* 170–173 (1950). An enzyme cleavable group can then be added to the remaining hydroxyl function at the 7 position. For example, β-D-galactopyranoside tetraacetate 3 is prepared by reaction of the phenolate anion of compound 2 with tetra-O-acetyl-α-D-galactopyranosyl bromide (available from Sigma Chemical Co., St. Louis, Mo.) using a procedure described by Baggett et al. in *Carbohydrate Research* 197, 295–301, (1990). The protected species then can be deprotected. As shown in Scheme 1, 7-(2,3,4,6-tetra-O-acetyl-β-D-galactopyranosyloxy)coumarin-4-acetate 3 is hydrolysed to give 7-β-D-galactopyranosyloxycoumarin-4-acetic acid 4 using the procedure described by Baggett et al. in *Carbohydrate Research* 197, 295–301, (1990). Compound 4 can then be modified with a suitable amine functional group to yield the final product. Scheme 1 demonstrates conversion of compound 4 to the pentafluorophenyl ester and then reaction with ethanolamine to give the compound 5. Compound 5 can also be obtained from compound 3 as outlined in Scheme 1.

While commercially available, compounds 1 and 2 can also be prepared, as shown below in Scheme 2, using the published method described by Baker, et al., *J. Chem. Soc.* 170–173 (1950) and Gray et al., *Analytica Chimica Acta*, 256, 111–115 (1992) respectively.

Scheme 2

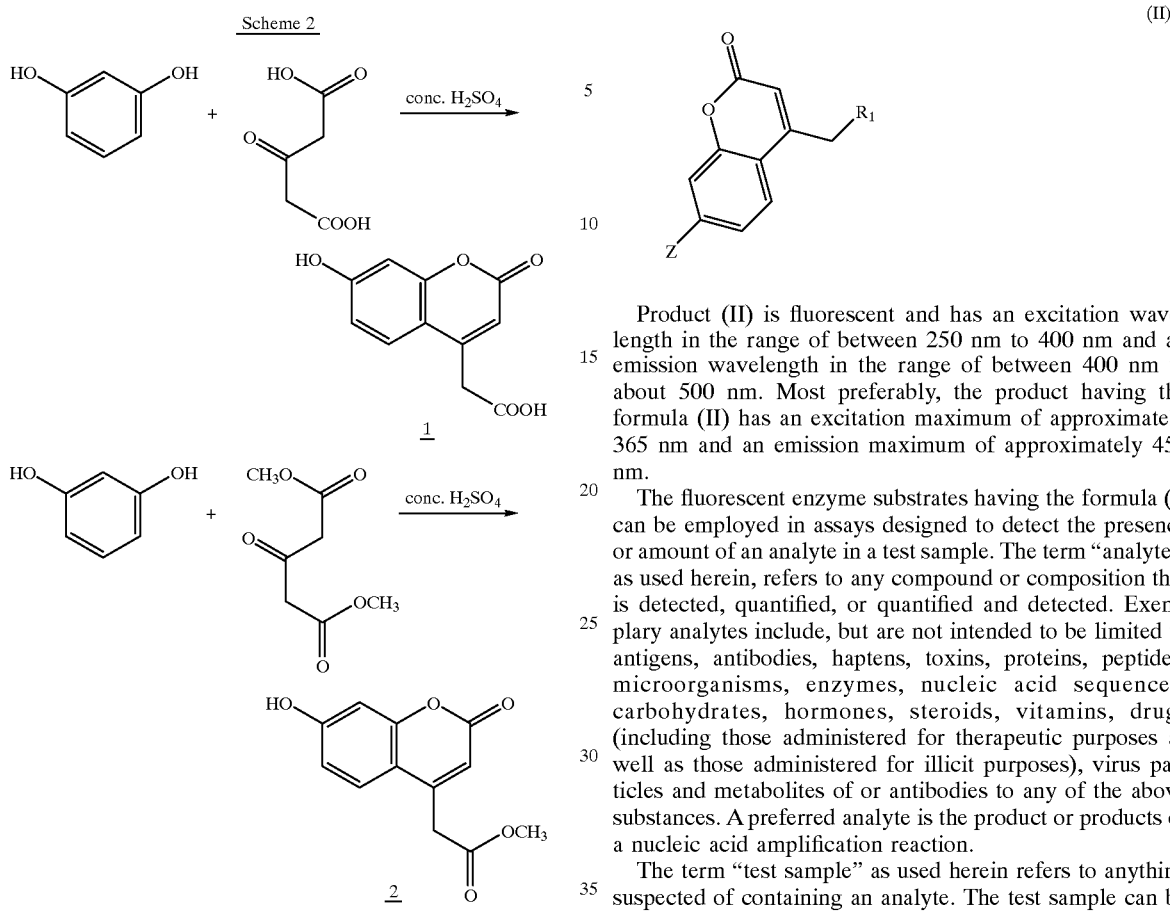

Fluorescent enzyme substrates having the formula (I) are water soluble and stable for extended periods of time at ambient or reduced temperatures. The solubility and stability characteristics of the substrate are a function of the side chains appended to the 4-position of coumarin. Substrates of the present invention have a water solubility of at least 1000 mg/L, preferably at least 2000 mg/L and, more preferably at least 2500 mg/L, and remain in solution for at least 2 weeks at ambient temperature and for at least 4 weeks at a temperature of 2–8° C. Preferably, the fluorescent enzyme substrates provided herein remain in solution for at least one month at the above temperature ranges. Additionally, the fluorescent enzyme substrates provided herein are stable and therefore do not break down to alternative chemical structures in solution.

In the presence of a suitable enzyme, the enzyme cleavable group herein designated R is cleaved from the compound (I) thereby leaving the fluorescent compound having the formula (II) shown below wherein $R^1$ and Z are defined above. Those skilled in the art will recognize that the group Z may be in protonated, unprotonated or a combination of protonated and unprotonated Z species, depending upon, for example, the pH of the medium containing the product (II).

(II)

Product (II) is fluorescent and has an excitation wavelength in the range of between 250 nm to 400 nm and an emission wavelength in the range of between 400 nm to about 500 nm. Most preferably, the product having the formula (II) has an excitation maximum of approximately 365 nm and an emission maximum of approximately 450 nm.

The fluorescent enzyme substrates having the formula (I) can be employed in assays designed to detect the presence or amount of an analyte in a test sample. The term "analyte", as used herein, refers to any compound or composition that is detected, quantified, or quantified and detected. Exemplary analytes include, but are not intended to be limited to antigens, antibodies, haptens, toxins, proteins, peptides, microorganisms, enzymes, nucleic acid sequences, carbohydrates, hormones, steroids, vitamins, drugs (including those administered for therapeutic purposes as well as those administered for illicit purposes), virus particles and metabolites of or antibodies to any of the above substances. A preferred analyte is the product or products of a nucleic acid amplification reaction.

The term "test sample" as used herein refers to anything suspected of containing an analyte. The test sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, cells, and the like, or fermentation broths, cell cultures, chemical reaction mixtures and the like. Test samples can be used (i) directly as obtained from the source or (ii) following a pre-treatment to modify the character of the sample. Thus, the test sample can be pre-treated prior to use by, for example, preparing plasma from blood, preparing liquids from solid materials, diluting viscous fluids, filtering liquids, distilling liquids, concentrating liquids, inactivating interfering components, adding reagents, and the like. Test samples also can be pretreated to digest, restrict or render double stranded nucleic acid sequences single stranded. Moreover, test samples may be pretreated to accumulate, purify, amplify or otherwise concentrate nucleic acid sequences that may be contained therein.

According to one embodiment, the presence or amount of an enzyme in a test sample can be determined. In accordance with this embodiment, the fluorescent enzyme substrate (I) can be designed such that the enzyme cleavable group R is a group that can be cleaved by the enzyme suspected of being in the test sample. Hence, upon addition of the fluorescent enzyme substrate, the enzyme will act upon the substrate and yield the fluorescent product (II). The presence of (II) can then be detected as an indication of the presence of the enzyme in the test sample. The amount of the enzyme in the test sample can be correlated to the rate at which (II) is accumulated in solution, as is well known in the art.

According to another embodiment, the presence or amount of an analyte such as, for example, an antigen in a test sample can be detected or quantified. Heterogeneous-sandwich assay techniques are well known in the art for such purposes and can be employed in conjunction with the fluorescent enzyme substrates (I). For example, a test sample can be contacted with a capture reagent comprising a binding member immobilized to a solid support material. As used herein, specific binding member means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; and the like. A "solid support material", as used herein, refers to any material which is insoluble, or can be made insoluble by a subsequent reaction. Solid support materials thus can be a latex, plastic, derivatized plastic, magnetic or non-magnetic metal, glass or silicon surface or surfaces of test tubes, microtiter wells, sheets, beads, microparticles, chips, and other configurations known to those of ordinary skill in the art. Hence, after contacting a test sample with a capture reagent, any analyte in the test is bound to the capture reagent to form capture reagent/analyte complexes.

The presence of the analyte immobilized on the capture reagent can then be detected with a "conjugate" comprising a specific binding member labeled with an enzyme capable of cleaving the enzyme cleavable group R from the fluorescent substrate (I). In particular, the capture reagent/analyte complexes can be contacted with a conjugate to thereby form capture reagent/analyte/conjugate complexes. The so-formed complexes can then be contacted with the substrate (I) and formation of the fluorescent product (II) can be detected as an indication of the presence or amount of the analyte on the capture reagent and therefore in the test sample.

It will be understood, of course, that the formation of the capture reagent/analyte/conjugate complexes can be accomplished in any combination of steps or all at once, before (i) such complexes are contacted with the substrate (I) and (ii) a signal is detected as an indication of the presence of the analyte in the test sample. Additionally, those skilled in the art will recognize that wash steps can also be employed according to the assays provided herein to, for example, separate excess reagents from those participating in the formation of the complexes.

Multiple analytes that may be present in a test sample can also be detected using the substrate of the present invention. U.S. patent application Ser. No. 08/362,036, filed Sep. 30, 1997, which is herein incorporated by reference describes methods and additional reagents that can be employed to detect multiple analytes in a test sample. In accordance with methods for detecting multiple analytes, the analytes are captured on multiple capture reagents specific for each analyte or single capture reagents specific for multiple analytes. The so-formed capture reagent/first and second analyte complexes are then detected by contacting the complexes with multiple conjugates specific for the different analytes. At least one of the conjugates will comprise an enzyme capable of converting the fluorescent enzyme substrate (I) to the fluorescent product (II). Other conjugates used according to this embodiment may comprise a specific binding member conjugated to a detectable moiety such as, for example, a fluorophore, chemiluminophore, or another enzyme which can act upon another fluorescent substrate that is distinct from the fluorescent enzyme substrate of the formula (I). Hence, upon contacting the capture reagent/first and second analyte complexes with the various conjugates, capture reagent/first analyte/first conjugate and capture reagent/second analyte/second conjugate complexes are formed. Signals from each of the conjugates can then be detected as an indication of the first and second analytes in the test sample. As alluded to above, U.S. patent application Ser. No. 08/362,036, filed Sep. 30, 1997, details methods for distinguishing signals such as, for example, distinguishing one rate dependent signal from another, as well as distinguishing rate from steady state signals.

For example, in cases where two analytes are detected, one of the conjugates used to detect a first analyte comprises an enzyme capable of cleaving the R group from the fluorescent enzyme substrate of the formula (I). A second conjugate used to detect a second analyte may comprise an enzyme capable of acting upon a fluorescent enzyme substrate distinct from the substrate provided herein. Preferably, the fluorescent products from the substrates have similar spectral properties. The signals from the fluorescent products can be distinguished by sequentially adding the substrates to the capture reagent/first analyte/first conjugate complexes and capture reagent/second analyte/second conjugate complexes. Hence, multiple analytes can thereby be detected. As with the methods for detecting a single analyte, the manner in which capture reagent/second analyte/second conjugate complexes or second capture reagent/second analyte/second conjugate complexes are formed can be in any order and before, after or concomitantly with the formation of capture reagent/first analyte/first conjugate complexes. Additionally, wash steps may be employed, as above, between any or all of the steps of the assay.

According to a preferred embodiment, fluorescent enzyme substrate herein provided is employed to detect the presence or amount of at least two nucleic acid sequences that may be present in a test sample. Accordingly, the analytes comprise nucleic acid sequences or are otherwise the products of a amplification reaction such as, for example, LCR which is described in European Patent Applications EP-A-320–308 and EP-A-439–182 and PCR which is described in U.S. Pat. Nos. 4,683,202 and 4,683,195 all of which are herein incorporated by reference. The presence or amount of amplified target sequences and/or sequences complementary to the target sequence in a solution can be detected in much the same manner as more traditional analytes described above. In accordance with this method, primer and/or probe seqeunces that are used to prime amplification or detect amplification products can be labeled with, for example, haptens that specifically bind a conjugate and a capture reagent.

The present invention further provides kits that contain a fluorescent enzyme conjugate (I) of the present invention. The kits may include, the substrate compound in solid form or dissolved in a suitable aqueous buffer. The kit may also contain other suitably packaged reagents and materials for using the substrate in a particular assay. By way of example, the kit may further include, nucleic acid amplification primers and/or nucleic acid probes, buffers, nucleotides, enzymes, conjugates, capture reagents and the like.

The Examples that follow illustrate preferred embodiments of the present invention and are not limiting of the claims and specification in any way.

EXAMPLE 1

Preparation of 7-β-D-galactopyranosyloxycoumarin-4-acetic acid-(2-hydroxyethyl)amide 5 (AUG)

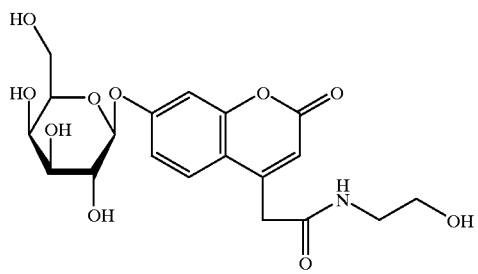

10 mg (0.026 mmoles) 7-β-D-galactopyranosyloxycoumarin-4-acetic acid 4 (prepared as described in Scheme 1) was dissolved in 2 ml of DMF (dimethyl formamide) and stirred under nitrogen ($N_2$). Pyridine (0.075 ml, 0.92 mmoles) was added to the above solution followed by pentafluorophenyl trifluoromethyl acetate (0.1 ml, 0.58 mmoles) and stirred for 3 hrs. The formation of the intermediate was confirmed by thin layer chromatography (TLC) (i-PrOH/EtOH/$NH_4$OH/water in ratio 60/35/5/20). The TLC plate was visualized by spraying a mixture of (anisaldehyde/$H_2SO_4$/EtOH/$CH_3$COOH in the ratio of 1/1/18/2 drops) and heating on a hot plate. The $R_f$ of intermediate was 0.53 and the $R_f$ of the starting carboxylic acid was 0.4. Ethanolamine (0.1 ml) was then added to the intermediate and stirred for 12 hrs. The formation of the amide was confirmed by TLC. The $R_f$ of the amide was 0.33. The reaction solvent was evaporated to dryness and the slightly yellowish residue was dissolved in 1.5 ml of 50/50 water/$CH_3$CN purified on a C-8 preparatory HPLC (high performance liquid chromatography) column using a gradient of 5/95 $CH_3$CN/water (0.1% TFA) to 30/70 $CH_3$CN/water (0.1% TFA) in 25.5 min. The peak eluting at 14 min. was collected and the solvent lyophilized to give 6 mg of a white fluffy powder giving a yield of 54%. $^1$HNMR (DMSO-$d_6$);δ 3.12 (q, 2H, $CH_2$—$CH_2$—OH), 3.39 (q, 2H, HN—$CH_2$—$CH_2$), 3.42–3.66 (m, 6H, H-2,3,4,5,6,6), 3.62 (s, 2H, coumarin—$CH_2$—), 4.71 (t, 1H, —$CH_2$—$CH_2$—OH), 4.99 (d, 1H, anomeric proton, $J_{1,2}$ of 7.8 Hz confirms β-configuration), 4.54, 4.67, 4.91, 5.24 (d,t,d,d, 1H,1H,1H,1H, 2—OH, 3—OH, 4—OH, 6—OH), 7.01 (dd, 1H, coumarin H-6), 7.04 (d, 1H, coumarin H-8), 7.6 (d, 1H, coumarin H-5), 8.26 (t, 1H, amide proton). Mass Spectroscopy (MS) (ESI): for Mol. Formula $C_{19}H_{23}NO_{10}$ Calcd. 425, H found (M+Na)$^+$448.

EXAMPLE 2

Preparation of 7-β-D-galactopyranosyloxycoumarin-4-acetic acid-(2-hydroxyethyl)amide 5 (AUG)

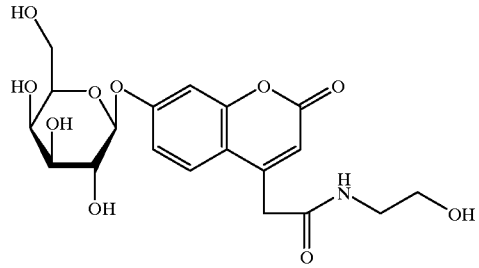

43 g (0.076 moles) of 7-(2,3,4,6-tetra-O-acetyl-β-D-galactopyranosyloxy)coumarin-4-acetate (i.e. compound 1 prepared as described in Scheme 1) was dissolved in 430 ml of methylene chloride in a 1 liter RB flask. 43 ml (0.712 moles) of ethanolamine was dissolved in 43 ml of methanol and added to the above solution. The solution was stirred at room temperature for 60 hrs and the resulting solid residue was filtered and washed with 50 ml of methylene chloride. The solid was suspended in 250 ml of methanol and stored in the freezer for 12 hrs. The solid was filtered again and suspended in 700 ml of methanol and refluxed for 30 min. The cloudy suspension was cooled to room temperature, then further cooled in an ice bath and filtered. The wet solid thus obtained was suspended in 200 ml of ether and stirred for 30 min., then filtered and vacuum dried at room temperature to give 12 g of an off-white solid. The yield was 37%. The structure was confirmed by $^1$H NMR and MS (as in Example 1).

Alternatively, the crude product is further purified by HPLC methods as described hereinbefore. Gravity or flash reverse phase methods of column chromatography may also be used with appropriate reverse phase (RP) solvent mixtures, such as $H_2O$/$CH_3OH$ or $H_2O$/$CH_3CN$, and gradients derived from combinations of these solvent ratios. Such gradients are generally from higher solvent polarity to lower solvent polarity (e.g. from 5/95 acetonitrile/water 0.1% TFA to 70 water/30 acetonitrile with 0.1 TFA). Trifluoroacetic acid (0.1%) may be used in such solvent mixtures as well.

EXAMPLE 3

Preparation of 7-β-D-galactopyranosyloxy coumarin-4-acetic acid-(2-methoxy ethyl) amide 6

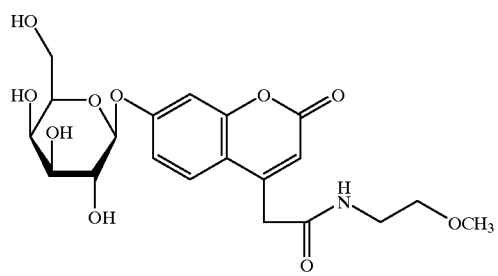

10 mg (0.026 mmoles) of 7-β-D-galactopyranosyloxycoumarin-4-acetic acid (i.e. compound 4 prepared as described in Scheme i) was dissolved in 1.6 ml of dry anhydrous DMF under nitrogen. Pyridine (0.075 ml, 0.92 mmoles) was added dropwise followed by the addition of pentafluorophenyltrifloroacetate (0.1 ml, 0.58 mmoles). The progress of the reaction was followed on a TLC plate by eluting with a mixture of i-PrOH/EtOH/NH$_4$OH/water (60/35/5/20). The R$_f$ of starting material (acid) was 0.4; and the R$_f$ of the reactive intermediate was 0.533. The TLC plate was visualized by spraying a mixture of (anisaldehyde/H$_2$SO$_4$/EtOH/CH$_3$COOH in the ratio 1/1/18/2 drops) and heating on a hot plate. After the formation of the intermediate (3 hrs), 3-methoxy ethylamine (0.1 ml, 0.8 mmoles) was added dropwise and left to stir at room temperature under N$_2$ for 12 hrs. The formation of the product was confirmed on TLC and the R$_f$ of amide product was 0.41. The DMF was evaporated on a rotary evaporator under vacuum at 40–45° C. After evaporating to dryness the residue was dissolved in 1 ml of 50/50 CH$_3$CN/water. The crude material was purified on a C-8 preparatory HPLC column using a gradient of 5/95 CH$_3$CN/water (0.1% TFA) to 30/70 CH$_3$CN/water (0.1% TFA) in 25.5 min. The peak eluting at 16 min was collected and the solvent lyophilized and the yield was 54%. The structure of the product was confirmed by $^1$H-NMR (CD$_3$)$_2$SO:δ 3.12 (t, 2H, CH$_2$—CH$_2$—OCH$_3$), 3.32 (m, 5H, HN—CH$_2$—CH$_2$—CH$_3$, CH$_2$—OCH$_3$), 3.36–3.66 (m, 6H, H-2,3,4,5,6,6), 4.99 (d, 1H, J$_{1,2}$ 7.8 Hz), J$_{1,2}$ of 7,8 Hz confirms β-configuration., 4.52, 4.54, 4.8, 5.45 (d,t,d,d, 1H, 1H, 1H, 1H, 2—OH, 3—OH, 4—OH, 6—OH), 6.38 (s, 1H, H-3), 7.0 (dd, 1H, H-6), 7.15 (d, 1H, H-8), 7.7 (d, 1H, H-5). MS: Mol. Formula. C$_{20}$H$_{25}$NO$_{10}$. Calcd. 439.21, observed (M+Na)$^+$462.0. Solubility in 0.1 mM Tris, 0.1 mM KCl pH 8.33: 1.5 mg/ml.

EXAMPLE 4

7-β-D-galactopyranosyloxycoumarin-4-acetic acid-carboxymethyl) amide 7

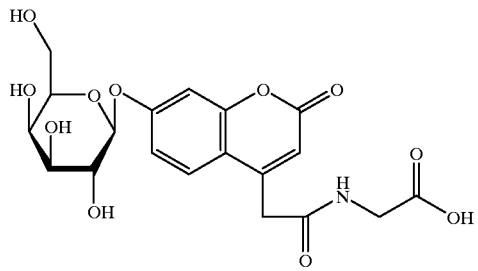

6 mg (0.0157 mmoles) of 7-β-D-galactopyranosyloxycoumarin 4-acetic acid (i.e. compound 4 prepared as described in Scheme I) was dissolved in 1 ml of dry DMF and stirred under nitrogen. Pyridine (0.058 g, 0.73 mmoles) was added dropwise, followed by pentafluorophenyl trifluoroacetate (0.130 g, 0.464 mmoles). The mixture was stirred at room temperature for 2 hrs and the formation of the active ester was confirmed by TLC. Glycine methyl ester hydrochloride (60 mg, 0.477 mmoles—available from Aldrich Chemical Co, Milwaukee, Wis.) was suspended in 0.5 ml of dry DMF and 70 mg of DBU (30 mmoles) was added, resulting in a clear solution. This solution was slowly added to the mixture containing the active ester (4) and stirred for an additional 2 hrs, with the formation of the product monitored on C-8 RP HPLC. After evaporating to dryness, the residue was dissolved in 1 ml 50/50 CH$^3$CN/water. The crude material was purified on a C-8 preparatory HPLC column using a gradient of 5/95 CH$_3$CN/water(0.1% TFA) to 30/70 CH$_3$CN/water(0.1% TFA) in 25.5 min. The product eluting at 14.9 min was collected and lyophilized. The ester was further hydrolyzed to the carboxylic acid derivative using aqueous 1N NaOH. TLC was conducted using a mixture of i-PrOH/EtOH/NH$_4$OH/water (60/35/5/20) and the R$_f$ of starting material (acid) was 0.4; and the R$_f$ of the reactive intermediate was 0.533. The R$_f$ of Glycine methyl ester derivative was 0.5; and the R$_f$ of Glycine carboxylic acid derivative was 0.4. The TLC plate was visualized by spraying a carbohydrate specific spray and visualizing on a hot plate. Characterization: MS: for C$_{19}$H$_{21}$NO$_{11}$ (Calc. 439.3, found (M+H)$^+$ 439.2. $^1$H-NMR (DMSO-d$_6$);δ 3.2–3.7 (m, 6H, H-2,3,4,5, 6,6), 3.75 (s, 2H, coumarin CH$_2$), 3.86 (d, 2H, NH—CH$_2$—CO), 4.98 (d, 1H, J$_{1,2}$ 8.1 Hz, H-1). The J$_{1,2}$ value of 8.1 Hz for the compound confirms the β configuration, 4.54 (d, 1H), 4.675 (t, C-6 OH), 4.91 (d, 1H), 5.23 (d, 1H), 6.36 (s, 1H, H-3 of coumarin), 7.0 (dd, 1H, H-6), 7.02 (d, 1H, H-8), 7.7 (d, 1H, H-5), 8.6 (t, 1H, CH$_2$—NH—CO).

EXAMPLE 5

Preparation of 7-β-D-galactopyranosyloxycoumarin-4-acetic acid methyl ester 8

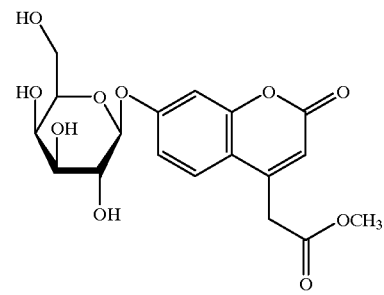

Compound 8 was prepared according to the procedure of Neil Baggett, Martin A. Case, Paul R. Darby, and Charles J. Gray, *Carbohydrate Research* 197, 295–301, (1990). Methanolic sodium methoxide (0.5 ml) was added to a solution of compound 3 from Scheme 1 (0.50 g, 0.89 mmol) in 30 ml of warm, dry methanol. The solution was stored for 1 hr at room temperature, then overnight at 5° C. The resulting pale-pink prisms were collected, washed with a little ice cold methanol, and recrystallised from water/ethanol (1:1) to give 8 (0.32 g: 87%), m.p. 128–129° C. The structure was confirmed by $^1$H NMR and MS.

EXAMPLE 6

Synthesis of 7-β-D-galactopyranosyloxycoumarin-4-acetic acid-(2-hydroxyethyl)amide 5 via P(Ph)₃/CCl₄ method

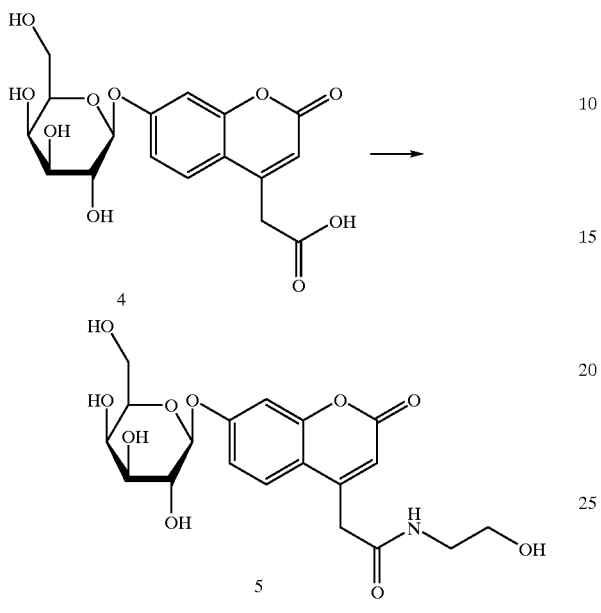

A mixture of 5 mg (0.013 mmoles) of 7-β-galactopyranosyloxy-coumarin-4-acetic acid 4 (prepared as described in Scheme 1), triphenyl phosphine (14 mg, 0.0533 mmoles) and ethanolamine (20 mg, 0.15 mmoles) was dissolved in 0.5 ml of dry DMF and stirred under $N_2$ at 100° C. for 12 hr. Carbon tetrachloride (0.4 ml) was added and further heated for 24 hr. After checking the completion of the reaction by C-8 RP-HPLC, the crude product was obtained by evaporating the DMF. The amide product was obtained by RP-HPLC purification and molecular weight of the desired product was confirmed by MS for $C_{19}H_{23}NO_{10}$, found $(M+H)^+426$ and $(M+NH_4)^+443$.

EXAMPLE 7

Preparation of 7-hydroxycoumarin-4-acetic acid-(2-hydroxyethyl) amide 9

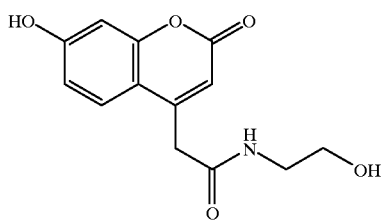

200 mg (0.85 mmole) of 7-hydroxycoumarin-4-methyl ester 2 (prepared as described in Scheme 1) was dissolved in 5 ml of dry DMF and stirred with 0.5 g (8.5 mmoles) of ethanolamine at room temperature for 52 hrs. The DMF was then evaporated from the dark brown solution. The residue obtained after further evaporation with methanol was dissolved in water and purified on a C-8 RP-HPLC column using a gradient of 5/95 $CH_3CN$/water (0.1% TFA) to 30170 $CH_3CN$/water (0.1% TFA) in 25.5 min. The peak eluting at 21.6 min was collected and lyophilized to give 0.16 g of an off-white powder MS: Mol. Formula, $C_{13}H_{13}NO_5$; Calculated: 263.26, found $(M+H)^+264.2$.

EXAMPLE 8

Preparation of 7-β-D-galactopyranosyloxycoumarin-⁴-acetic amino alcohol or amino ether derivatives 10–15

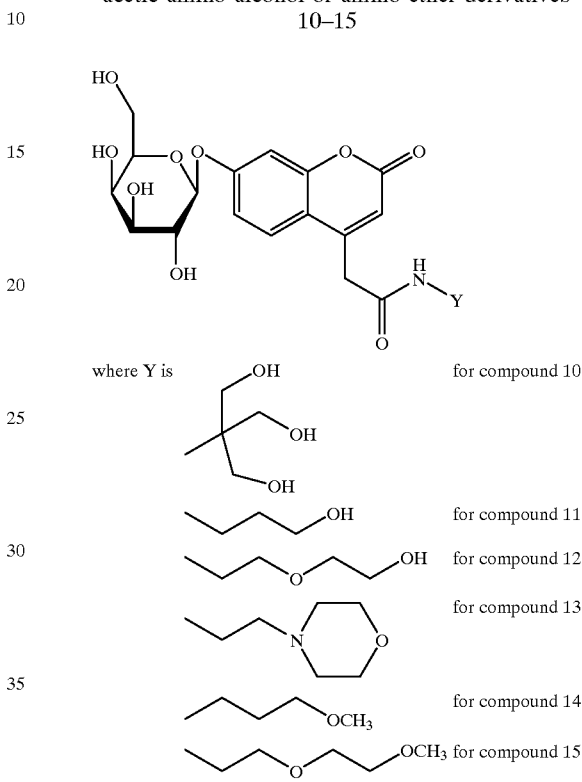

Compounds 10–15 are synthesized starting from compound 4 (prepared as described in Scheme 1) as follows: approximately 10 mg (0.026 mmoles, 1.0 equivalents) of 7-β-D-galactopyranosyloxycoumarin-⁴-acetic acid (4 ) is dissolved in 2 ml of DMF and stirred under $N_2$ or Ar. Pyridine (0.075 ml, 0.92 mmoles) is added to the above solution followed by pentafluorophenyl trifluoromethyl acetate (0.1 ml, 0.58 mmoles, 22 equivalents) and stirred for approximately 2.5 hrs. The formation of the intermediate is confirmed using TLC by eluting with a mixture of i-PrOH/EtOH/NH₄OH/water with ratios as determined appropriate by methods well known to those skilled in the art. The TLC plate is visualized by spraying with a carbohydrate specific reagent mixture.

Note that for the synthesis of compounds 10–12, the hydroxyl group of the respective amino alcohol can be protected as an acetate functionality (Scheme 3). For example, conversion of amino alcohol to a protected amine can be effected by the use of benzyl chloroformate (Greene, T. W., Protective Groups in *Organic Synthesis*, John Wiley & Sons, 1981, pg. 239). The resultant CBZ protected amine is then esterified with acetic anhydride (or alternatively acid halide) as described in Greene, T. W., *Protective Groups in Organic Synthesis*, John Wiley & Sons, 1981, pg. 53 and references contained therein. Paladium/carbon catalyzed hydrogenation is then performed to remove the CBZ group as also described in Greene, T. W., *Protective Groups in Organic Synthesis*. John Wiley & Sons, 1981, pg. 239.

Scheme 3

H₂N~~O~~OH →

Cbz-HN~~O~~OH →

Cbz-HN~~O~~OCCH₃ →

H₂N~~O~~OCCH₃

After the active ester is generated as described above, 10–30 equivalents of an amine (shown below), is then added and stirred for 6–24 hours.

[Amine structures:]
- H₂N–C(CH₂OAc)₃ Or H₂N–C(CH₂OH)₃  for compound 10
- H₂N~~OAc Or H₂N~~OH  for compound 11
- H₂N~~O~~OAc Or H₂N~~O~~OH  for compound 12
- H₂N~~N(morpholine)  for compound 13
- H₂N~~OCH₃  for compound 14
- H₂N~~O~~OCH₃  for compound 15

The formation of the amide is confirmed by the TLC difference between the $R_f$ of the obtained product and $R_f$ of the starting material. In the cases where the hydroxyl is protected, the acetate (10–12) functionality is hydrolyzed in the presence of a base to yield the final product. The reaction solvent is evaporated to dryness and the residue is dissolved in 0.5–2.5 ml of approximately 50/50 water/CH₃CN or other appropriate chromatographic solvent, and purified on a C-8 or C-18 preparatory RP-HPLC column using isocratic or gradient methods. Other methods such as precipitation or crystallization may also be used as well. The appropriate peak eluting from the column or product obtained by precipitation from solution is identified and collected. Excess solvent is then removed by lyophilization to yield a powder. Identity is determined by ¹H NMR, elemental analysis, Mass Spectroscopy and other methods well known to those skilled in the art.

Other amino alcohols, amino ethers or amino thioethers can also be substituted in place of those listed. Generically, this procedure is used to produce the amide product corresponding to the amine starting material by (a) first converting the carboxylic acid moiety of intermediate 4 (from Scheme 1) to the corresponding amide via the in situ conversion of the carboxylic acid to the pentafluorophenyl activated ester, followed by (b) acylation of the activated ester by the corresponding amine.

EXAMPLE 9

Preparation of 7-β-D-galactopyranosyloxycoumarin-4-acetic amino alcohol or amino ether derivatives 1–15

[Structure: 7-β-D-galactopyranosyloxycoumarin-4-acetamide with N–Y substituent]

where Y is:
- –C(CH₂OH)₃  for compound 10
- ~~OH  for compound 11
- ~~O~~OH  for compound 12
- ~~N(morpholine)  for compound 13
- ~~OCH₃  for compound 14
- ~~O~~OCH₃  for compound 15

Alternatively, compounds 10–15 are synthesized as follows from compound 3 (from Scheme 1) by the following method. 43 g (0.076 moles, 1.0 equivalents) of 7-(2,3,4,6-tetra-O-acetyl-β-D-galactopyranosyloxy)coumarin-4-acetate (i.e. compound 3 prepared as described in Scheme 1) is dissolved in 300–700 ml of methylene chloride in a 1–2 liter RB flask. 43 ml (0.712 moles, 10.0 equivalents) of an amine shown below:

- H₂N–C(CH₂OH)₃  for compound 10
- H₂N~~OH  for compound 11
- H₂N~~O~~OH  for compound 12
- H₂N~~N(morpholine)  for compound 13
- H₂N~~OCH₃  for compound 14
- H₂N~~O~~OCH₃  for compound 15 is dissolved in approximately 42 ml of methanol and added to the above solution. The solution is stirred at room temperature for about 60–120 hrs and the resulting solid residue is filtered and washed with 20–200 ml of methylene chloride. The solid is suspended in 100–500 ml of methanol and stored in the freezer for 6–72 hrs. The solid is filtered again and suspended in 500–1000 ml of methanol and refluxed for about 30 min. The cloudy suspension is cooled to room temperature, then further cooled in an ice bath and filtered. The wet solid thus obtained is suspended in about 100–300 ml of ether and stirred for about 30 min, then filtered and vacuum dried at room temperature to give several grams of white solid. The structure is confirmed by $^1$H-NMR and MS.

Other amino alcohols, amino ethers or amino thioethers can also be substituted in place of those listed. Generically, this procedure is used to produce the amide product corresponding to the amine starting material by converting the ester moiety of intermediate 3 (from Scheme 1) to the corresponding amide via the acylation of the carboxylic ester.

EXAMPLE 10

Synthesis of amino acid derivatives of 7-β-D-galactopyranosyloxycoumarin-4-acetic acid 16–19

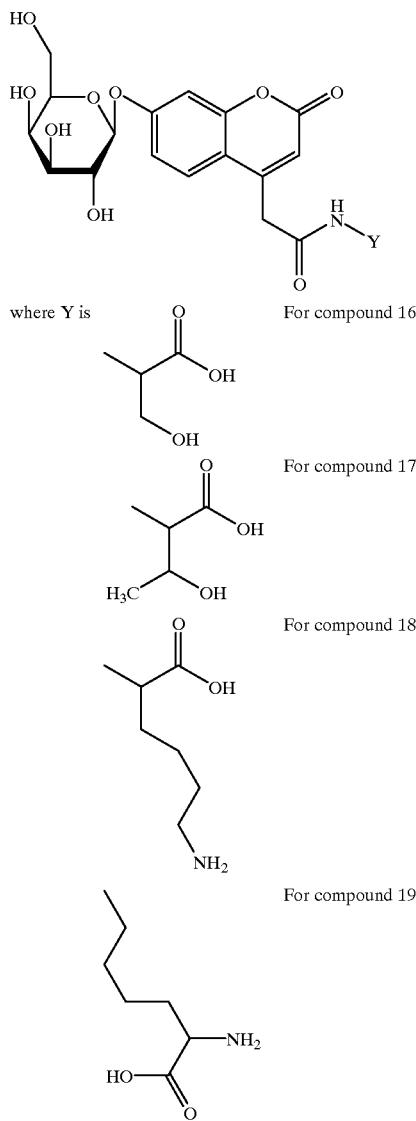

6 mg (0.0157 mmoles, 1.0 equivalents) of 7-β-D-galactopyranosyloxycoumarin 4-acetic acid 4 (prepared as described in Scheme 1) is dissolved in about 1 ml of dry DMF and stirred under nitro-en. Pyridine (0.058 g, 0.73 mmoles, 13.0 equivalents) is added dropwise, followed by the dropwise addition of pentafluorophenyl trifluoroacetate (0.130 g, 0.464 mmoles, 30 equivalents). The mixture is stirred at room temperature for 1–6 brs and the formation of the active ester is confirmed by TLC. The appropriate methyl ester hydrochloride of amino acids selected from:

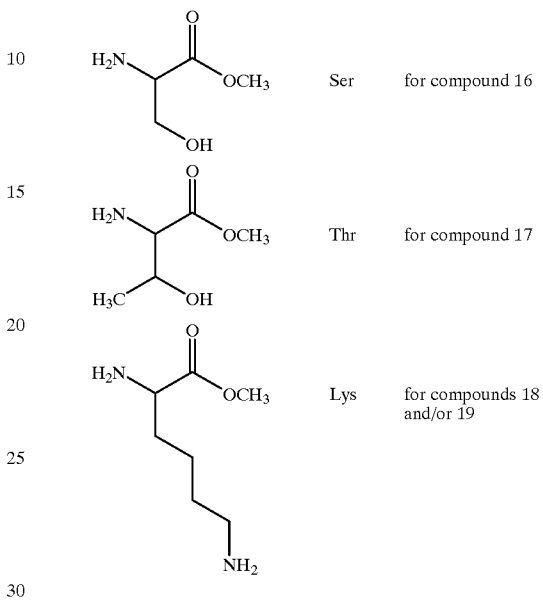

is suspended in approximately 0.5 ml of dry DMF and 70 mg of DBU (0.486 m, 30 equivalents) is added to result in a clear solution. This solution is slowly added to the mixture containing the pentafluorophenyl active ester (generated in situ) and is stirred for approximately an additional 2 hrs. The formation of the product is monitored on C-8 RP-HPLC, C-18 HPLC, TLC or other appropriate analytical method. After evaporating to dryness, the residue is dissolved in about 1 ml of 50/50 CH$_3$CN/water. The crude material is purified on a C-8 preparatory HPLC column or other appropriate chromatographic support using a gradient or isocratic system. The isolated product is obtained by either lyophilization, precipitation, crystallization or removal of solvent in vacuo. The ester is further hydrolyzed to the corresponding carboxylic acid derivative using aqueous 1N NaOH. TLC is conducted using a mixture of i-PrOH/EtOH/NH$_4$OH/water at ratios selected to give appropriate resolution of starting, material from product. The TLC plate is visualized by spraying a carbohydrate specific spray or other appropriate stain and developed a hot plate. The product is characterized by MS, NNM and CHN analysis. Separation of the two possible products (compound 18 or 19) is accomplished using chromatographic techniques such as those described above. NMR is used to make a determination of the exact structure in order to distinguish compound 18 from compound 19. Alternatively, the α and ε CBZ protected analogs of lysine can be used for condensation with compound 4 to produce compounds 18 and 19 respectively after deprotection with Pd/H$_2$ or alternate methods described in Example 8.

Other amino acid esters can also be substituted in place of those listed. Generically, this procedure is used to produce the amide product corresponding to the amine starting material by (a) first converting the carboxylic acid moiety of intermediate 4 (from Scheme 1) to the corresponding amide via the in situ conversion of the carboxylic acid to the pentafluorophenol activated ester, followed by (b) acylation of the activated ester by the corresponding amine. The ester protecting group, is then removed via hydrolysis (as described in Example 10) to yield the final water soluble enzyme substrate.

EXAMPLE 11

Preparation of 7-β-D-galactopyranosyloxycoumarin-4-acetic amino polyamine derivatives 20–22

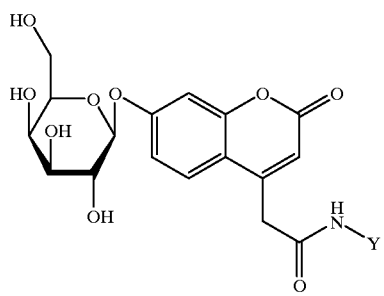

where Y is

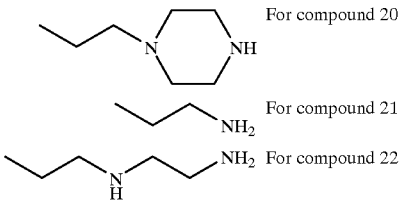

Compounds 20–22 are synthesized starting from compound 4 (from Scheme 1) as follows: 10 mg (0.026 mmoles, 1.0 equivalent) 7-β-D-galactopyranosyloxycoumarin-4-acetic acid 4 (from Scheme 1) is dissolved in 2 ml of DMF and stirred under $N_2$ or Ar. Pyridine (0.075 ml, 0.92 mmoles) is added to the above solution followed by pentafluorophenyl trifluoromethyl acetate (0.1 ml, 0.58 mmoles, 22 equivalents) and stirred for about 1–5 hours. The formation of the intermediate is confirmed using TLC by eluting with a mixture of i-PrOH/EtOH/$NH_4$OH/water in appropriate ratios. The TLC plate is visualized with the aid of a carbohydrate specific spray or methods well known to those skilled in the art. Around 15–30 equivalents of a diamine or polyamine selected from the group below:

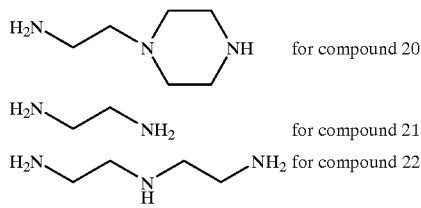

is then added and stirred for 6–24 hrs. An excess of the amine reagent should be used to avoid dimer formation and thus reduced yield of the desired product. The formation of the amide is confirmed by the TLC difference between the $R_f$ of the obtained product and $R_f$ of the starting material. The reaction solvent is evaporated to dryness and the residue is dissolved in 0.5–2.5 ml of approximately 50/50 water/$CH_3CN$ and purified on a C-8 or C-18 RP preparatory HPLC column using isocratic or gradient methods. Other methods such as precipitation or crystallization may be used as well. The appropriate peak eluting from the column or precipitated from solution is identified using MS or UV spectroscopy and collected. Excess solvent is then removed by lyophilization to yield a solid or oil when chromatographic methods are used. Alternatively, filtration or other similar methods are used to isolate a solid from a liquid when precipitation or crystallization methods are used. Identity is determined by proton NMR, elemental analysis, and mass spectroscopy.

Other polyamines can also be substituted in place of those listed. Generically, this procedure is used to produce the amide product corresponding to the amine starting material by (a) first converting the carboxylic acid moiety of intermediate 4 (from Scheme 1) to the corresponding amide via the in situ conversion of the carboxylic acid to the pentafluorophenol activated ester, followed by (b) acylation of the activated ester by the corresponding amine. The ester protecting group, is then removed via hydrolysis (as described in Example 11) to yield the final water soluble enzyme substrate polyamine derived amide.

EXAMPLE 12

Preparation of 7-β-D-galactopyranosyloxycoumarin-4-acetic amino polyamine derivatives 20–23

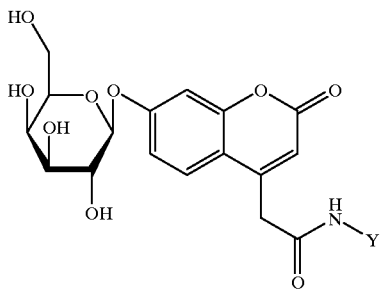

where Y is

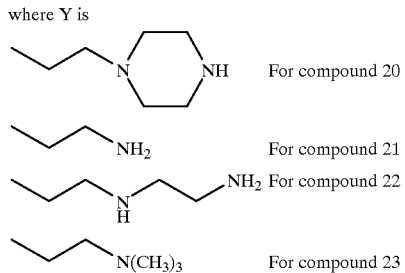

Compounds 20–23 are synthesized from compound 3 (from Scheme 1) by the following method: 43 g (0.076 moles, 1.0 equivalent) of 7-(2,3,4,6-tetra-O-acetyl-β-D-galactopyranosyloxy)coumarin-4-acetate 3 (prepared as described in Scheme 1) is dissolved in 300–700 ml of methylene chloride in a 1–2 liter RB flask. 43 ml (0.712 moles, 10.0 equivalents) of an amine selected from the following:

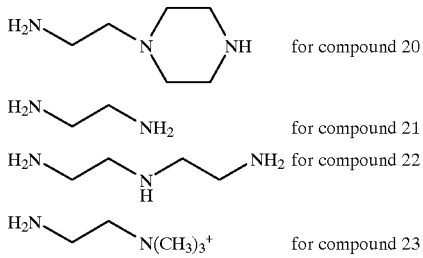

is dissolved in around 42 ml of methanol and added to the above solution. The solution is stirred at room temperature for about 60–120 hrs and the resulting solid residue is filtered and washed with 20–200 ml of methylene chloride. The solid is suspended in 100–500 ml of methanol and stored in the freezer for 6–72 hrs. The solid is filtered again and suspended in 500–1000 ml of methanol and refluxed for about 30 minutes. The cloudy suspension is cooled to room temperature, then cooled further in an ice bath and filtered. The wet solid thus obtained is suspended in about 100–300 ml of ether and stirred for about 30 min, then filtered and vacuum dried at room temperature to give several grams of white solid. The structure is confirmed by $^1$H NMR and MS.

Other polyamines can also be substituted in place of those listed. Generically, this procedure is used to produce the amide product corresponding to the amine starting material by converting the ester moiety of intermediate 3 to the corresponding amide via the acylation of the carboxylic ester.

EXAMPLE 13

Preparation of 7-β-D-galactopyranosyloxycoumarin-4-acetic taurine derivative

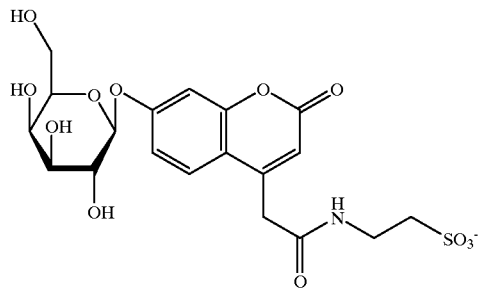

24

Compound 24 is synthesized starting from compound 4 (from Scheme 1) as follows:

10 mg (0.026 mmoles, 1.0 equivalents) 7-β-D-galactopyranosyloxycoumarin-4-acetic acid 4 (from Scheme 1) is dissolved in approximately 2 ml of DMF, or other suitable solvent, and stirred under N$_2$ or Ar. Pyridine (0.075 ml, 0.92 mmoles) is added to the above solution followed by pentafluorophenyl trifluoromethyl acetate (0.1 ml, 0.58 mmoles, 22 equivalents) and stirred for about 1–5 hrs. The formation of the intermediate is confirmed using TLC by eluting with a mixture of i-PrOH/EtOH/NH$_4$OH/water in appropriate ratios. The TLC plate is visualized by spraying a mixture of (anisaldehyde/H$_2$SO$_4$/EtOH/CH$_3$COOH) in the ratio 1/1/18/2 drops and heating on a hot plate. Around 15–30 equivalents of taurine (Aldrich Chemical Co., Milwaukee, Wis.) is then added and stirred for 6–24 hrs. The formation of the amide is confirmed by the TLC difference between the R$_f$ of the obtained product and R$_f$ of the starting material. The reaction solvent is evaporated to dryness and the residue is dissolved in 0.5–2.5 ml of around 50/50 water/CH$_3$C N or other appropriate chromatographic solvent and purified on a C-8 or C-18 RP preparatory HPLC column using isocratic or gradient. Other methods such as precipitation or crystallization may also be used. The appropriate peak eluting from the column or precipitated from solution is identified by MS or UV spectroscopy and collected. Excess solvent is then removed by lyophilization or other appropriate method to yield a powder. Alternatively, filtration or other similar methods are used to isolate a solid from a liquid when precipitation or crystallization methods are used. Identity is determined by $^1$H NMR, elemental analysis, mass spectropscopy and other methods well known to those skilled in the art.

Other aminosulfonic acids can also be substituted in place of those listed. Generically, this procedure is used to produce the amide product corresponding to the amine starting material by (a) first converting the carboxylic acid moiety of intermediate 4 (from Scheme 1) to the corresponding amide via the in situ conversion of the carboxylic acid to the pentafluorophenol activated ester, followed by (b) acylation of the activated ester by the corresponding amine. The ester protecting group, is then removed via hydrolysis (as described in Example 10) to yield the final water soluble enzyme substrate amino sulfonic acid derived amide.

EXAMPLE 14

Preparation of 7-β-D-galactopyranosyloxycoumarin-4-acetic taurine derivative 24

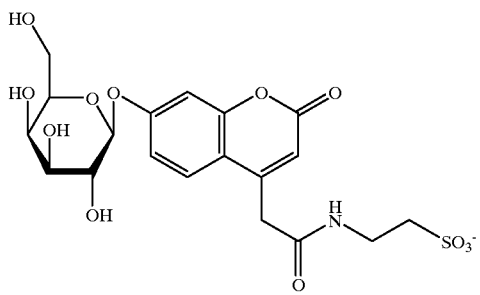

24

Compound 24 is synthesized from compound 3 (from Scheme 1) by the following method: 43 g (0.076 moles, 1.0 equivalents) of 7-(2,3,4,6-tetra-O-acetyl-β-D-galactopyranosyloxy)coumarin-4-acetate 3 (prepared as described in Scheme 1) is dissolved in 300–700 ml of methylene chloride, or other suitable solvent, in a 1–liter RB flask. 43 ml (0.712 moles, 10.0 equivalents) of taurine (Aldrich Chemical Co., Milwaukee, Wis) is dissolved in around 42 ml of methanol and added to the above solution. The solution is stirred at room temperature for about 60–120 hrs and the resulting solid residue is filtered and washed with 20–200 ml of methylene chloride. The solid is suspended in 100–500 ml of methanol and stored in the freezer for 6–72 hrs. The solid is filtered again and suspended in 500–1000 ml of methanol and refluxed for about 30 minutes The cloudy suspension is cooled to room temperature, then cooled further in an ice bath and filtered. The wet solid thus obtained is suspended in about 100–300 ml of ether and stirred for about 30 min, then filtered and vacuum dried at room temperature to give several grams of white solid. The structure is confirmed by $^1$H NMR and MS.

Other aminosulfonic acids can also be substituted in place of those listed. Generically, this procedure is used to produce the amide product corresponding to the amine starting material by converting the ester moiety of intermediate 2 (from Scheme 1) to the corresponding amide via the acylation of the carboxylic ester group carbonyl.

EXAMPLE 15

Preparation of 7-β-D-galactopyranosyloxycoumarin-4-acetic poly amino acid derivatives 25–26

25

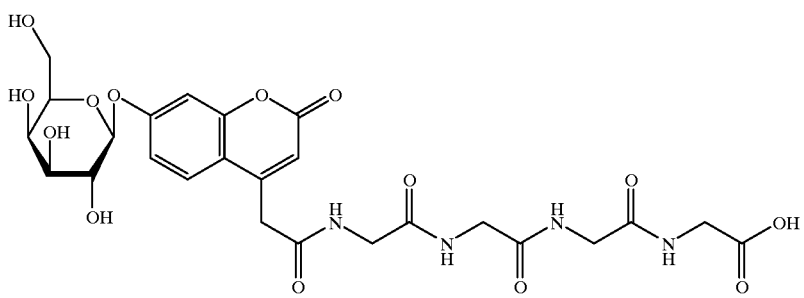

26

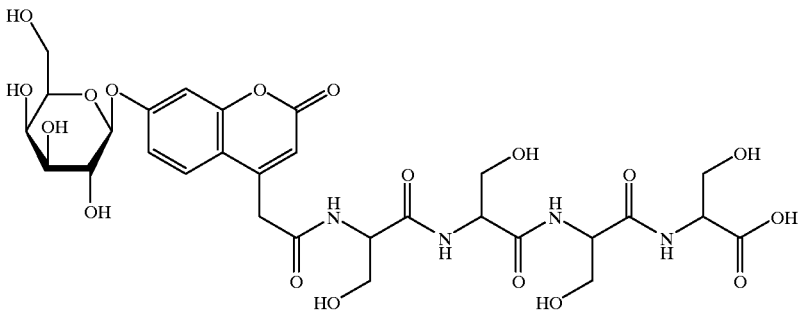

Compounds 25–26 are synthesized by adapting the procedures described in Example 4 such that the appropriate polymeric amino acid side chain residue is substituted for residues listed in Example 4. Other polyaminoacids (either homo or heteropolymeric) can also be substituted in place of those listed. Generically, this procedure is used to produce the amide product corresponding to the amine starting material by converting the ester moiety of intermediate 3 (from Scheme 1) to the corresponding amide via the acylation of the carboxylic ester or by (a) first converting the carboxylic acid moiety of intermediate 4 (from Scheme 1) to the corresponding amide via the in situ conversion of the carboxylic acid to the pentafluorophenol activated ester, followed by (b) acylation of the activated ester by the corresponding amine. Alcohols and or carboxylic acid moieties can be protected, if necessary, to improve synthesis yield during coupling chemistries where side reactions may result. Ester protecting groups are then hydrolyzed as described in previous examples (e.g. Example 4) to produce the corresponding water soluble β-galactosidase coumarin substrate.

EXAMPLE 16

Preparation of 7-hydroxycoumarin-4-acetic acid amide. compounds 27–43

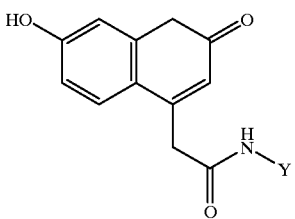

-continued

Where Y is

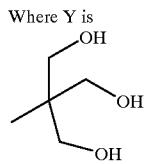

For compound 27

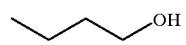

For compound 28

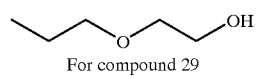

For compound 29

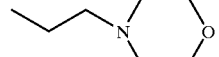

For compound 30

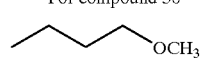

For compound 31

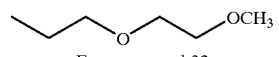

For compound 32

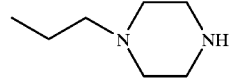

For compound 33

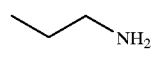

For compound 34

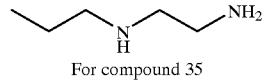

For compound 35

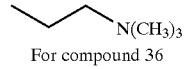

For compound 36

-continued

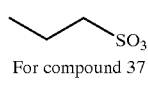
For compound 37

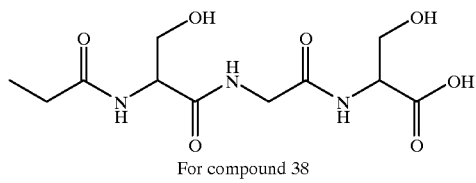
For compound 38

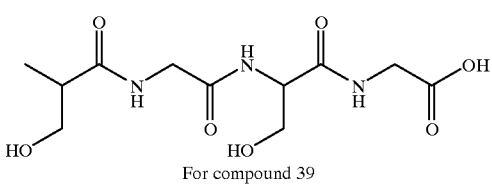
For compound 39

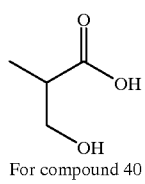
For compound 40

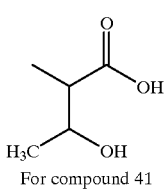
For compound 41

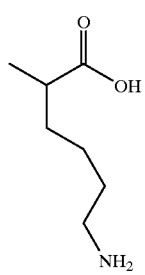
For compound 42

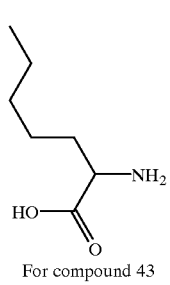
For compound 43

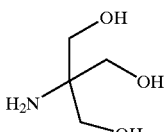
For compound 27

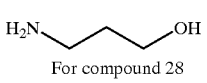
For compound 28

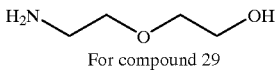
For compound 29

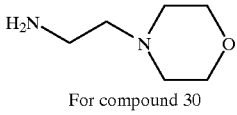
For compound 30

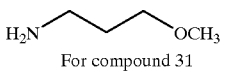
For compound 31

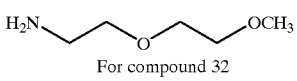
For compound 32

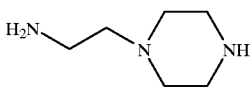
For compound 33

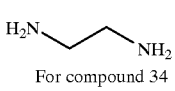
For compound 34

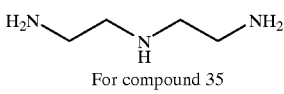
For compound 35

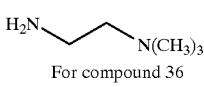
For compound 36

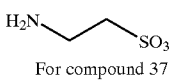
For compound 37

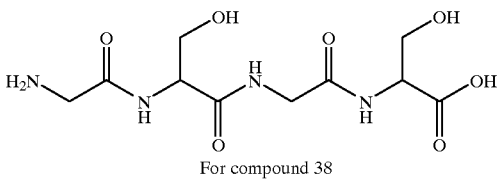
For compound 38

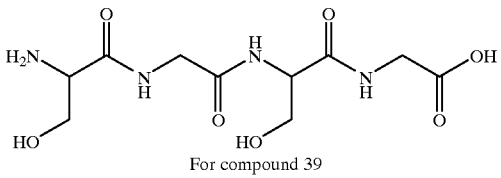
For compound 39

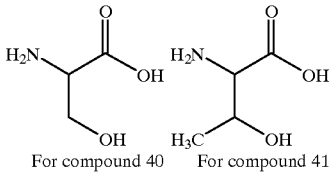
For compound 40  For compound 41

0.85 mmole of 7-hydroxycoumarin-4-methyl ester 2, prepared as described in Scheme 1, is dissolved in approximately 5 ml of dry DMF and stirred at room temperature for 20–60 hrs with approximately 8.5 mmoles (10 equivalents) of an amine shown below:

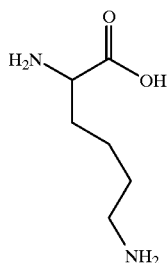

For compound 42 or 43

The DMF is then evaporated from the usually dark brown solution. The residue obtained after further evaporation with methanol is dissolved in water 5 and purified on a RP C-8 HPLC column using a gradient of around 5/95 CH₃CN/water (0.1% TFA) to 30/70 CH₃CN/water (0.1% TFA) or other suitable mixtures. The appropriate peak is collected and lyophilized to give an off-white powder. This material corresponds to the product of the enzyme substrate reaction with the appropriate respective enzyme (e.g. β-galactosidase, alkaline phosphatase, phosphotriesterase, glucoronidase). Similarly, other amines can be used in order to produce structures with other R groups added for solubility of the product of the enzyme substrate. Generally, protection of alcohols is not required, but yields can be improved upon by utilizing such protection/deprotection sequences as those described in Examples 4, 8 and 10. Mild hydrolysis conditions are then used in order to obtain the desired product as also described in Examples 4, 8 and 10.

EXAMPLE 17

Synthesis of 7-(Dialkylphosphate)-4-acetic acid-(2-methoxyethyl)amides. 44–49. highly water soluble substrates for phosphotriesterase

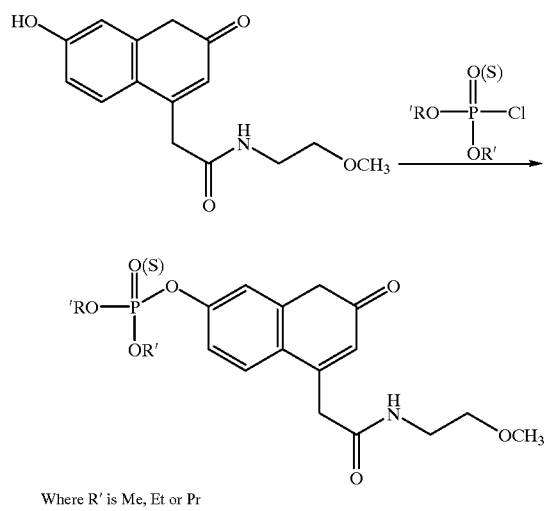

Where R' is Me, Et or Pr

To a solution containing 1.39 g (5 mmoles) of 7-Hydroxy-4-acetic acid (2-methoxyethyl)amide compound 31 (synthesized as described in Example 16) in 10 ml of dry CH₂Cl₂, 5 mmoles dialkyl chlorophosphate (Aldrich) is added and stirred under nitrogen. Compound 44, 45 and 46 are ultimately synthesized when the alkyl group is methyl, ethyl or propyl respectively. Compounds 47, 48 and 49 are ultimately synthesized when the alkyl group is methyl, ethyl or propyl respectively and dialkyl chlorophophosphate reagent is substituted with dialkyl chlorothiophosphate. Diisopropylethylamine (1.29 g, 10 mmoles) in 3 ml of methylene chloride is slowly added dropwise to the product of the phosphorylation reaction and mixed overnight at room temperature. The reaction mixture in methylene chloride is extracted with 3 ml 1% HCl, 3 ml water, and the organic layer dried over magnesium sulfate. After filtration and removal of the solvent, crude product is purified on silica gel column with approximately 50/50 hexane/ethyl acetate. Product is characterized by TLC, NMR and MS. This synthesis is outlined in the scheme below.

EXAMPLE 18

Synthesis of 7-(phosphate)-4-acetic acid-(2-methoxyethyl)amides 50–51, highly water soluble substrates for alkaline phosphatase

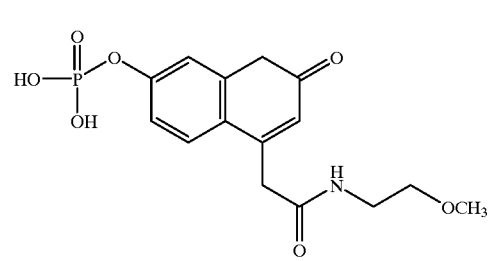

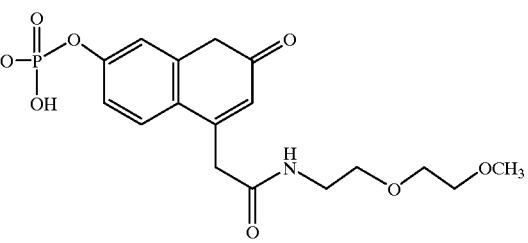

Compounds 50 and 51 are synthesized from compounds 31 and 32 respectively, described in Example 16. After the synthesis of the appropriate corresponding coumarin ethers, the phosphate is synthesized using methods described in *Tetrahedron*, 47, 3895 (1991) and *Carbohydrate Research*, 229, 332 (1992). Alternatively, this synthesis is adapted to synthesize alkaline phosphatase substrates based on various other amino ethers by substituting analogues such as compounds 31–37 as described in Example 16.

EXAMPLE 19

Synthesis of lipase and esterase substrates 52–55

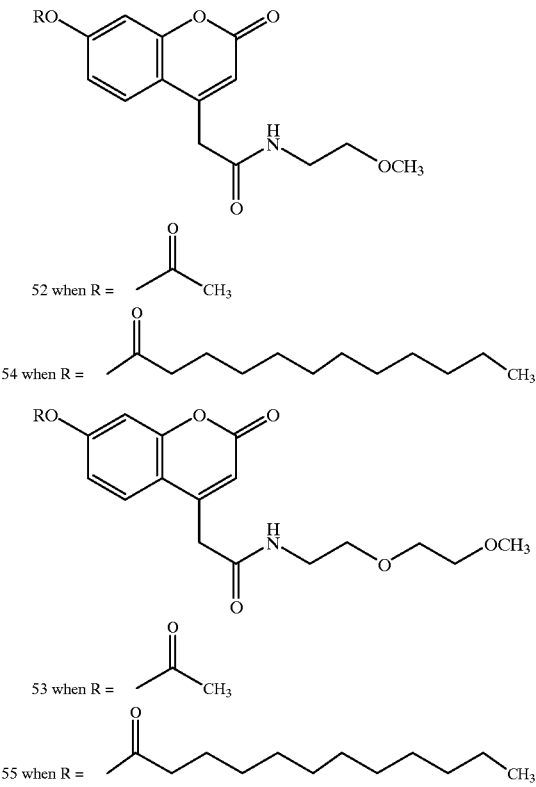

Synthesis of lipase and esterase substrates 52–55 is accomplished using appropriate analogues (as described in Examples 18 and 7) as starting materials followed by the conversion to the above phenolic esters according to acylation methods. For compounds 52 and 53, acetic acid chloride is the acylation agent and for compounds 54 and 55, myristyl (undecanoic) acid chloride is the acylation agent. The compounds are purified by extraction or column chromatography. For examples of acylation procedures, see Greene, T. W., *Protective Groups in Organic Synthesis*, John Wiley & Sons (1981) under protecting groups for alcohols. Acylation using activated carboxylic acid groups of alkyl carboxylic acids is used to generate other long chain alkyl derivatives, similar in structure to compounds 54 and 55, that are more specific for lipase rather than generic esterases. Other esterase substrates are made by using various other alkyl carboxylic acid groups and are obtainable from the Aldrich Chemical Company. These carboxylic acids are then activated to reactive acyl chlorides by means such as, for example, thionyl and the synthesis sequence, as described above, carried out to produce the final esterase product.

EXAMPLE 20

Synthesis of 7-hydroxycoumarin-4-acetic acid amide 29 and β-galactosidase susbtrate 12

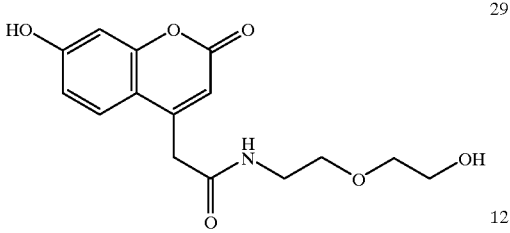

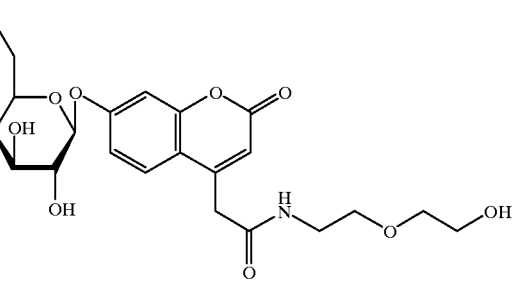

0.250 g (0.00106 mmoles) of 7-hydroxycoumarin-4-acetic acid methyl ester 2 (from Scheme 1) was dissolved in 5 ml of DMF. 2-(2-aminoethoxy)ethanol (1.118 gm, 0.0106 mmoles) was dissolved in 1 ml of DMF and added to the above solution and stirred under $N_2$ for 60 h at room temperature. The DMF was evaporated under vacuo at 80° C. The resulting thick oil was dissolved in water and purified on C-8 RP-HPLC using a gradient system of 5/95 AcCN/Water to 60/40 AcCN/water over 40 min. The peak eluting at 23 min. was collected and lyophilized to give 0.176 g of a white fluffy solid representing a yield of 54%. MS: for $C_{15}H_{17}NO_6$, $(M+Na)^+$ 330.3. $^1H$ NMR confirmed the structure of compound 29. Compound 12 is synthesized by the conversion of the phenolate anion to the glycosidic ether linkage as described in Scheme 1. Hydrolysis of the acetyls is then accomplished also as described in Scheme 1 to yield the highly water soluble enzyme substrate 12.

EXAMPLE 21

Synthesis of 7-ethoxy-4-acetic acid-(2-methoxyethyl)amide-coumarin 56–58. substrates for microsomal dealkylase

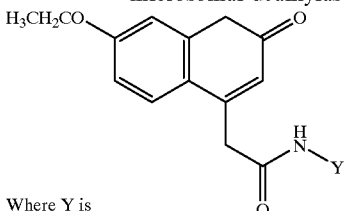

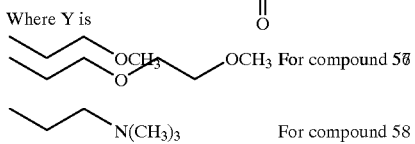

Synthesis of microsomal dialkylase substrates 56, 57 and 58 is accomplished using, compounds 31, 32 and 37 as the corresponding respective precursors. The preparation of these compounds is described in Example 16. The phenolate anion of each of these starting materials (i.e. compounds 31, 32 and 37) is reacted with bromoethane (available from Aldrich) using, methods described in *Carbohydrate Research*, 197, 295–301, (1990), or *Organic Synthesis* (J. Wiley&Sons) col. vol. III, p.140.

EXAMPLE 22

Stability and performance of 4-methylumbelliferyl β-D-galactopyranoside (MUG)

The commercially available substrate 4-methylumbelliferyl β-D-galactopyranoside (MUG, catalogue # M-1489, Molecular Probes, Eugene, Oreg.) for the enzyme β-galactosidase was evaluated for stability and performance using the Abbott LCx® system (available from Abbott Laboratories, Abbott Park, Ill.).

In particular, MUG was evaluated using two "calibrators". The first calibrator (Calibrator E) contained approximately $2 \times 10^{10}$ molecules/100 µl of a double stranded DNA sequence designated SEQ. ID. No. 1. One strand of the double stranded DNA sequence was labeled with carbazole at the 5' end and dansyl at the 3' end. The complementary strand was labeled with carbazole at the 3' end and dansyl at the 5' end. Thus, when these strands are hybridized to one another, two carbazoles are present at one end of the double stranded sequence, and two dansyl are present at the other end of the double stranded sequence. The individual strands of the double stranded sequence were synthesized using standard oligonucleotide synthesis methodology and haptenated with carbazole and dansyl using standard cyanoethyl phosphoramidite coupling chemistry such as that described in U.S. Pat. No. 5,464,746, which is herein incorporated by reference. The double stranded sequence (SEQ. ID, No. 1) was diluted in 50 mM EPPS, 0.5 mM EDTA, 41 mM KOH, pH 7.6 containing 0.05% Polysorbate-20 and 0.1% NaN$_3$ to its final concentration of approximately $2 \times 10^{10}$ molecules to yield Calibrator E. Another calibrator (Calibrator A) containing 0 molecules of the double stranded DNA sequence was also prepared as a negative control. Calibrator A contained 50 mM EPPS, 0.5 mM EDTA, 41 mM KOH, pH 7.6 and 0.05% Polysorbate-20 and 0.1% NaN$_3$.

The calibrators were employed to evaluate the performance of 0.6 mM MUG in 0.1 M Tris-HCl, pH 8.3 that had been variably treated and/or stored. Specifically, one aliquot of the MUG solution was frozen and thawed (F/T) 3 times prior to storage at 2 to 8° C. Another aliquot of the MUG solution was maintained at room temperature and the last MUG solution was stored at 2 to 8° C. without a freeze-thaw treatment. The initial MUG solution was tested, in triplicate, shortly after its production (at time 0). All MUG solutions were tested in duplicate after storage for 12 and 23 days. Precipitate formed in the solutions stored at 2 to 8° C. but no precipitate was observed in the solution stored at room temperature. As a result, for solutions in which a precipitate was observed, the solutions were tested both before and after filtration of the solution to remove the precipitate.

The following procedure was employed to test the various MUG solutions. 150 µl from the various solutions was pipetted into the predilution well of an IMx® reaction cell (available from Abbott Laboratories, Abbott Park, Ill.) and 100 µl of Calibrator E was added to the sample well of the IMx® reaction cell. The calibrator was detected on the Abbott LCx® system using (i) a suspension of anti-carbazole polyclonal antibody coated microparticles at 0.06% solids in 21.9 mM Tris, 28.2 mM Tris (hydroxymethyl)aminomethane HCl, 100 mM NaCl, pH 8.0 containing 13.6% sucrose, and 0.1% NaN$_3$, and (ii) anti-dansyl monoclonal antibody/β-D-galactosidase conjugate at 1 mg/ml in 24 mM Tris, 400 mM NaCl, 125.6 mM Tromethane HCl, 20 mM MgCl$_2$, 0.1 mM Zinc Chloride, pH 7.4 containing 10% D-Mannitol, 10% BRIJ-35, 3% Bovine serum albumin, 0.1% Sodium Alkyl Paraben, and 0.0005% sarafloxacin hydrochloride (a quinolone anti-microbial described in U.S. Pat. No. 5,284,776). The LCx® automatically performed the following procedure: 40 µl of antibody coated microparticles were mixed with 50 µl of sample (Calibrator E) in the reaction well of the IMx® reaction cell. 110 µl of LCx® Dilution Buffer (commercially available from Abbott Laboratories, Abbott Park, Ill.) was then added and the mixture was incubated for approximately 8.5 minutes, allowing the anti-carbazole coated microparticles to bind and form a complex with the carbazole on the Calibrator E reagent. 150 µl of this mixture was then added to the filter tab of the IMx® reaction cell, followed by the addition of 50 µl of the antibody conjugate to the filter tab. This was incubated for 5 minutes during which the anti-dansyl antibody conjugate would bind to the dansyl on any calibrator which had previously complexed with the microparticle. The filter tab was then washed 4 times with 50 µl of LCx® Dilution Buffer, and 70 µl of the substrate solution was added to the filter tab. After 2 seconds the rate of conversion of substrate to product was measured and reported as counts/second/second (c/s/s). Results from the MUG testing are shown below in Table 1.

TABLE 1

| Storage | Mean LCx ® Performance of MUG (c/s/s) | | |
|---|---|---|---|
| | Day 0 | Day 12 | Day 23 |
| Room Temperature | 690.5 | 622.3 | 631.3 |
| 2–8° C. unfiltered | | 491.4 | 503.9 |
| 2–8° C. filtered | | 449.5 | 423.3 |
| F/T, 2–8° C. unfiltered | | 544.7 | 619.0 |
| F/T, 2–8° C. filtered | 536.4 | 547.9 | |

As shown by Table 1, all of the MUG substrate solutions showed a moderate to significant signal decrease after storage at 2–8° C. (whether or not frozen and thawed) due to substrate precipitation. Additionally, filtration of the solution also appeared to result in a slight loss of signal.

The stability and performance of MUG in variety of different buffers was also evaluated by (i) visual inspection for the formation of a precipitate after storage in clear glass vials and (ii) performance using the procedures described above. The composition of the various buffers, as well as the concentration of MUG in these buffers, is shown in Table 2. An aliquot of each buffer was subject to three different conditions. Specifically, one aliquot of each buffer was (i) stored at room temperature, (ii) stored at 2–8° C., and (iii) frozen and thawed up to three times. Performance in the LCx® was determined (as above) for each of the various solutions prior to being split and subjected to the three different conditions. Performance was considered either acceptable (+) or unacceptable (−). Table 2 does not show precipitation data for the MUG solutions stored at room temperature because no precipitate was observed in any of these solutions. However, it is noted that precipitate was observed in other MUG solutions stored at room temperature that had MUG concentrations above 0.6 mM.

TABLE 2

| Solution | LCx® Performance | Precipitation 2–8° C. | F/T |
|---|---|---|---|
| 0.6 mM MUG, 0.1M Tris, 125 mM NaCl, 2 mM MgCl$_2$, pH 8.3 | + | 3 wks | ND |
| 0.5 mM MUG, 0.1M Tris, 125 mM NaCl, 2 mM MgCl$_2$, pH 8.3 | + | 11 mos | ND |
| 0.4 mM MUG, 0.1M Tris, 125 mM NaCl, 2 mM MgCl$_2$, pH 8.3 | + | 11 mos | ND |
| 0.3 mM MUG, 0.1M Tris, 125 mM NaCl, 2 mM MgCl$_2$, pH 8.3 | + | 11 mos | ND |
| 0.2 mM MUG, 0.1M Tris, 125 mM NaCl, 2 mM MgCl$_2$, pH 8.3 | − | 11 mos | ND |
| 0.6 mM MUG, 0.1M Tris, pH 8.3 | + | 1 wk | + |
| 0.5 mM MUG, 0.1M Tris, pH 8.3 | + | 3 wks | ND |
| 0.4 mM MUG, 0.1M Tris, pH 8.3 | − | 11 mos | ND |
| 0.3 mM MUG, 0.1M Tris, pH 8.3 | − | 11 mos | ND |
| 0.2 mM MUG, 0.1M Tris, pH 8.3 | − | 11 mos | ND |
| 0.4 mM MUG, 0.1M Tris, pH 8.3 | − | 10 wks | ND |
| 0.2 mM MUG, 0.1M Tris, pH 8.3 | − | No (21 wks) | ND |
| 0.1 mM MUG, 0.1M Tris, pH 8.3 | − | No (21 wks) | ND |
| 0.4 mM MUG, 0.1M Tris, 2% DMSO, pH 8.3 | − | 10 wks | ND |
| 0.6 mM MUG, 0.1M Tris, 125 mM NaCl, 2 mM MgCl$_2$, pH 8.3 | + | 4 wks | ND |
| 0.6 mM MUG, 0.1M Tris, 125 mM NaCl, 2 mM MgCl$_2$, 5% EtOH, pH 8.3 | + | 4 wks | + |
| 0.6 mM MUG, 0.1M Tris, 125 mM NaCl, 2 mM MgCl$_2$, 15% EtOH, pH 8.3 | + | 4 wks | + |
| 0.6 mM MUG, 0.1M Tris, 125 mM NaCl, 2 mM MgCl$_2$, 25% EtOH, pH 8.3 | − | 4 wks | ND |
| 0.6 mM MUG, 0.1M Tris, 125 mM NaCl, 2 mM MgCl$_2$, pH 8.3 | + | No (7 wks) | + |
| 0.6 mM MUG, 0.1M Tris, 125 mM NaCl, 2 mM MgCl$_2$, pH 7.7 | + | No (7 wks) | + |
| 0.6 mM MUG, 0.1M Tris, 125 mM NaCl, 2 mM MgCl$_2$, pH 7.1 | − | No (7 wks) | + |
| 0.6 mM MUG, 0.1M MES, 125 mM NaCl, 2 mM MgCl$_2$, pH 6.8 | − | No (7 wks) | + |
| 0.6 mM MUG, 0.1M MES, 125 mM NaCl, 2 mM MgCl$_2$, pH 6.2 | − | 5 wks | + |
| 0.6 mM MUG, 0.1M MES, 125 mM NaCl, 2 mM MgCl$_2$, pH 5.6 | − | No (7 wks) | + |
| 0.6 mM MUG, 0.1M Tris, 125 mM NaCl, 2 mM MgCl$_2$, 0.1 mg/ml BSA, 0.5% Tween-20, pH 8.3 | + | 5 wks | + |
| 0.6 mM MUG, 0.1M Tris, 125 mM NaCl, 2 mM MgCl$_2$, 1% DMSO, pH 8.3 | + | 5 wks | + |
| 0.6 mM MUG, 0.1M Tris, 125 mM NaCl, 2 mM MgCl$_2$, 1% DMSO, 0.1 mg/ml BSA, 0.5% Tween-20, pH 8.3 | + | 7 wks | + |
| 0.4 mM MUG, 0.1M Tris, 125 mM NaCl, 2 mM MgCl$_2$, 1% DMSO, pH 8.3 | + | No (14 wks) | + |
| 0.4 mM MUG, 0.1M Tris, 125 mM NaCl, 2 mM MgCl$_2$, 2% DMSO, pH 8.3 | + | No (14 wks) | + |
| 0.6 mM MUG, 0.1M Tris, 125 mM NaCl, 2 mM MgCl$_2$, 5% glycerol, pH 8.3 | + | 7 wks | ND |
| 0.6 mM MUG, 0.1M Tris, 125 mM NaCl, 2 mM MgCl$_2$, 2% DMSO, pH 8.3 | + | 6 wks | ND |
| 0.6 mM MUG, 0.1M Tris, 125 mM NaCl, 2 mM MgCl$_2$, 2% DMSO, 0.5% Tween-20, pH 8.3 | + | 2 wks | ND |
| 0.6 mM MUG, 0.1M Tris, 125 mM NaCl, 2 mM MgCl$_2$, 4% DMSO, pH 8.3 | + | 2 wks | ND |

ND = not determined

As stated above, precipitation results for MUG stored at room temperature in the listed buffers is not shown because no precipitation was observed in the solutions stored at room temperature. The precipitation data in the "2–8° C." column is presented as the amount of time elapsed after the solutions were prepared before a precipitate was observed (unless "No" is indicated in which case the amount of time the study was conducted is given). The data in the F/T column is given as a positive sign (+) in cases where a precipitate was observed after the 1–3 F/T cycles (unless "ND" is indicated in which case, as stated above, results were not determined). Table 2 also shows that the performance of MUG as a substrate appeared to be dependent upon the substrate concentration as well as the buffer composition. In particular, MUG appeared to be more soluble in buffers containing organic solvents (e.g. DMSO or ethanol), but such solvents inhibit enzymatic activity. Additionally, MUG appeared more soluble in buffers having a high pH but such pHs inhibit β-galactosidase activity. Finally, while lower concentrations of MUG were soluble, LCx® rates decreased with a decreasing MUG concentration.

EXAMPLE 23

Performance of 3-carboxyumbelliferyl β-D-galactopyranoside (CUG)

The performance of commercially available 3-carboxyumbelliferyl β-D-galactopyranoside (CUG, catalogue #C-1488, Molecular Probes, Eugene, Oreg.) was evaluated as a fluorescent substrate for the enzyme β-D-galactosidase on the Abbott LCx® system. CUG was prepared at 0.6 mM, 1 mM, 1.5 mM and 2 mM in 0.1 M Tris-HCl, 125 mM NaCl, 2 mM MgCl$_2$, pH 8.3, or in 0.1 N Borate, 0.1 N KCl, pH 8.3. Each substrate solution was tested on the Abbott LCx® system using Calibrators A and Calibrator E in triplicate as described in Example 22. MUG solutions (0.6 mM) were also prepared in the Tris and Borate buffers described above (represented in Table 3 as "salt") as well as in 0.1 M Tris-HCl, pH 8.3 (with no MgCl$_2$ or NaCl-represented in Table 3 as "no salt"), and used for purposes of comparing the results from the CUG solutions. Results are shown in Table 3.

TABLE 3

| | | Mean LCx ® Performance (c/s/s) | | | | | |
|---|---|---|---|---|---|---|---|
| | | CUG Concentration | | | | 0.6 mM MUG | |
| Buffer | Sample | 0.6 mM | 1.0 mM | 1.5 mM | 2.0 mM | salt | no salt |
| Tris | Cal A | 6.2 | 8.8 | 10.7 | 11.2 | 19.0 | 15.3 |
| | Cal E | 330.9 | 410.6 | 490.9 | 515.1 | 1124.3 | 708.8 |
| Borate | Cal A | 5.9 | 7.5 | 9.2 | 10.1 | 21.4 | ND |
| | Cal E | 288.4 | 416.1 | 489.1 | 531.2 | 1210.1 | ND |

ND = not determined

Although the CUG signal increased as the concentration of CUG was increased, MUG provided a higher signal at similar concentrations.

Additionally, MUG generated higher signals in buffers containing $MgCl_2$ and NaCl.

EXAMPLE 24

Performance of Compound 4 (CAUG)

The performance of CAUG (Compound 4) was evaluated for use as a substrate for the enzyme β-D-galactosidase on the Abbott LCx® system using Calibrator E and Calibrator A described above in Example 22. CAUG was diluted to 0.625 mM, 1.25 mM, 2.5 mM and 5 mM in 0.1 N Borate, 0.1 N KCl, pH 8.3 and tested in triplicate. A solution of 0.6 mM MUG in 0.1 M Tris-HCl, pH 8.3 was also prepared (as in Example 23) and tested using both calibrators. The results from this experiment is shown in Table 4.

TABLE 4

| | Mean LCx ® Performance (mean c/s/s) | | | | |
|---|---|---|---|---|---|
| | CAUG Concentration | | | | MUG |
| Sample | 0.625 mM | 1.25 mM | 2.5 mM | 5.0 mM | 0.6 mM |
| Calibrator A | 2.3 | 2.6 | 3.9 | 4.8 | 12.8 |
| Calibrator E | 94.2 | 159.0 | 223.0 | 256.8 | 602.1 |

As shown by Table 4, the signal increased slightly as the concentration of CAUG was increased. Additionally, MUG demonstrated a higher signal at similar or lower concentrations as compared to CAUG. As shown by Table 4, higher concentrations of CAUG did not yield a desirable rate on the LCx®.

In particular, the above experiment was then repeated using CAUG at 2.5 mM in different buffers to determine if signal could be increased by diluting CAUG in different buffers and increasing the concentration of CAUG in these buffers. The buffers tested were (i) 0.1 M Tris-HCl, 125 mM NaCl, 2 mM $MgCl_2$, pH 8.3 and (ii) 0.1 N Borate, 0.1 N KCl, pH 8.3 containing 1 mM β-Cyclodextrin (available from American Maizo Co.; Hammond, Ind.). Calibrator E was tested in triplicate with CAUG and in replicates of 4 with MUG; Calibrator A was tested in duplicate with CAUG in Tris, in a single replicate with CAUG in Borate and in replicates of 4 with MUG.

TABLE 5

| | Mean LCx ® Performance (c/s/s) | | |
|---|---|---|---|
| Sample | CAUG in Tris/salt | CAUG in Borate | MUG in Tris |
| Calibrator A | 4.6 | 4.0 | 12.4 |
| Calibrator E | 219.7 | 210.2 | 617.6 |

The results in Table 5 indicated that the selected buffers and increased concentrations did not significantly increase the signal obtained and therefore did not yield a desirable signal. The signal obtained with CAUG in the borate buffer was slightly improved after the original CAUG compound was repurified, but the improvement was not statistically significant.

EXAMPLE 25

Performance of MUG. CUG and CAUG with Increased Conjugate Concentration

This example was designed to determine if an increase in β-galactosidase conjugate would produce a higher signal with the substrates MUG, CUG and CAUG. The following substrate formulations were used: i) 0.6 mM MUG in 0.1 M Tris-HCl, pH 8.3; ii) 2.0 mM CUG in 0.1 M Borate, 0.1 N KCl, 1 mM β-cyclodextrin, pH 8.3; and iii) 2.5 mM CAUG in 0.1 M Borate, 0.1 N KCl, 1 mM β-cyclodextrin, pH 8.3. The β-galactosidase conjugate was used at concentrations of 1.0 µg/ml, 1.5 g/ml, 2.0 µg/ml, and 2.5 µg/ml. Calibrators A and E (as described above) were employed again in this experiment. Calibrator A was tested in duplicate and Calibrator E was tested in replicates of four, with testing performed as in Example 22.

TABLE 6

| | | Mean LCx ® Performance (c/s/s) | | | |
|---|---|---|---|---|---|
| | | Conjugate Concentration | | | |
| Substrate | Calibrator | 1.0 µg/ml | 1.5 µg/ml | 2.0 µg/ml | 2.5 µg/ml |
| MUG | A | 6.5 | 8.6 | 10.8 | 14.1 |
| | E | 496.1 | 566.3 | 600.3 | 667.6 |
| CUG | A | 5.5 | 6.5 | 8.4 | 10.4 |
| | E | 323.8 | 383.7 | 394.6 | 434.6 |
| CAUG | A | 2.1 | 2.8 | 3.5 | 4.2 |
| | E | 158.9 | 185.6 | 200.3 | 214.4 |

As shown by the results in Table 6, an increase in signal was observed for all substrates as the conjugate concentration was increased. MUG, however, provided greater signals at all conjugate concentrations while the signals obtained for CUG and CAUG did not reach a level that was desirable for the LCx®.

EXAMPLE 26

Performance of SMUG—Compound 8

SMUG (Compound 8) was synthesized as described in Example 5 and evaluated for use as a substrate for the enzyme β-D-galactosidase on the Abbott LCx® system as described in Example 22. Two SMUG solutions were tested. The first solution was 2.5 mM SMUG in 0.1 M MES, pH 6.5 MES (Shown below in Table 7 as "MES pH 6.5"), and the second was 2.5 mM SMUG in 0.1 M Tris, 125 mM NaCl 2 mM $MgCl_2$ at pH 7.0, 7.5, 8.0, and 8.5 (Shown below in Table 7 as "Tris pH at pH 6.5, 7.0, 7.5, 8.0, or 8.5"). Each of the above solutions was tested shortly after preparation (at time 0), then approximately 5 days later after the solutions were first stored at 46° C. for 50 hrs and then stored an additional 63 hours at 2–8° C. The solutions were tested as above in Example 22. Calibrator A was tested in duplicate and Calibrator E was tested in replicates of four, the results shown in Table 7 are averages from the replicates.

TABLE 7

| | | Mean LCx ® Performance (c/s/s) | | | | |
|---|---|---|---|---|---|---|
| Time | Calibrator | MES pH 6.5 | Tris pH 7.0 | Tris pH 7.5 | Tris pH 8.0 | Tris pH 8.5 |
| 0 | A | 8.4 | 11.8 | 17.9 | 19.8 | 19.4 |
| | E | 449.9 | 648.2 | 988.2 | 1158.9 | 1154.0 |
| 5 Days | A | 6.3 | 9.7 | 15.0 | 18.4 | 14.7 |
| | E | 437.5 | 568.6 | 844.6 | 861.1 | 728.3 |
| % Decrease in c/s/s for calibrator E | | 2.8 | 12.3 | 14.5 | 25.7 | 36.9 |

Table 7 shows that as pH increased up to 8.0, so did the signal from the substrate. However when tested 5 days later, the signal at the higher pH's decreased more than the signal at the lower pH's. HPLC analysis of samples from the stored solutions indicated that SMUG had degraded over time.

SMUG was then tested at pH 7.0 in different buffers to assess performance and stability over time. Three solutions of SMUG were prepared and stored at 45° C. for the duration of the experiment. The first solution was 2.5 mM SMUG in 0.1 M MES, pH 7.0; the second solutions was 2.5 mM SMUG in 0.1 M MOPS pH 7.0 and the third solution was 2.5 mM SMUG in 0.1 M. HEPES, pH 7.0. The substrate solutions were tested shortly after preparation (at time 0) and then weekly for 4 weeks. Calibrator A and Calibrator E were used to test the solutions as in Example 22 and samples run with Calibrator A were run in duplicate and samples run with Calibrator E were run in replicates of four. All values that are reported in Table 8 are averages of the replicates.

TABLE 8

| | | Mean LCx ® Performance (c/s/s) | | | | |
|---|---|---|---|---|---|---|
| Buffer | Calibrator | 0 | 1 week | 2 weeks | 3 weeks | 4 weeks |
| MES | A | 17.5 | 12.5 | 11.7 | 11.4 | 10.5 |
| | E | 815.8 | 689.6 | 595.5 | 517.6 | 519.0 |
| % Decrease in c/s/s for Calibrator E | | 0 | 15.5 | 27.0 | 36.6 | 36.4 |
| MOPS | A | 15.2 | 14.4 | 12.5 | 13.1 | 12.7 |
| | E | 818.3 | 736.8 | 625.6 | 561.2 | 563.2 |
| % Decrease in c/s/s for Calibrator E | | 0 | 10.0 | 23.5 | 31.4 | 31.2 |
| HEPES | A | 17.2 | 15.2 | 11.4 | 11.6 | 11.8 |
| | E | 841.4 | 730.8 | 572.7 | 508.5 | 557.0 |
| % Decrease in c/s/s for Calibrator E | | 0 | 13.1 | 31.9 | 39.6 | 33.8 |

As shown by Table 8, all buffer SMUG solutions showed decreased signal over time.

EXAMPLE 27

Performance of Compounds 5 and 6

A. Performance Using Calibrators AUG (Compound 5) was synthesized as described Examples 1, 2 or 6, and Compound 6 was synthesized as described in Example 3. Both amides were evaluated for use as a substrate for the enzyme β-D-galactosidase on the Abbott LCx® system as described in Example 22 using one replicate of Calibrator A and duplicates of Calibrator E. Both amides were tested at 3.0 mM, 2.5 mM, 1.0 mM and 0.5 mM in 0.1 M Tris, 125 mM NaCl, 2 mM $MgCl_2$, pH 8.3 and compared to 0.6 mM MUG in the same buffer, with Calibrator E tested in triplicate. The results in Table 9 show that both amides perform well at concentrations of at least 2.5 mM.

TABLE 9

| | Mean LCx ® Performance (c/s/s) | | | | | | | | |
|---|---|---|---|---|---|---|---|---|---|
| | Compound 5 (AUG) | | | | Compound 6 | | | | MUG |
| Cal | 3 mM | 2.5 mM | 1 mM | 0.5 mM | 3 mM | 2.5 mM | 1 mM | 0.5 mM | 0.6 mM |
| A | 24 | 20 | 14 | 10 | 23 | 22 | 14 | 10 | 14 |
| E | 978 | 1004 | 648 | 429 | 1006 | 989 | 736 | 481 | 788 |

Cal = Calibrator

The stability of compound 5 and compound 6 was evaluated by visually checking for precipitation (on a weekly basis) in solutions containing the compounds. The solutions were stored at 2 to 8° C. after being frozen and thawed (F/T) 6 times prior to storage at 2 to 8° C. The solutions themselves contained 2.5 mM compound 5 or compound 6 in 0.1 M Tris, 125 mM NaCl, 2 m $MgCl_2$, pH 8.3. These solutions were also evaluated for use as substrates on the LCx® system, as in Example 22, prior to the first F/T cycle, immediately after the six F/T cycles, and after six F/T cycles and then storage at 2 to 8° C. for 4 and 15 weeks. Testing was done using duplicates of Calibrator E and single replicates of Calibrator A (except for the last time point which was tested in duplicate). All reported values are an average of the replicates.

No precipitation was observed after storage under any of the conditions tested and the LCx® performance values are given in Table 10.

TABLE 10

| | Mean LCx ® Performance (c/s/s) | | | | | | | |
|---|---|---|---|---|---|---|---|---|
| | Compound 5 (AUG) | | | | Compound 6 | | | |
| Cal | 0 | 6 F/T | 4 wks | 15 wks | 0 | 6 F/T | 4 wks | 15 wks |
| A | 20.8 | 23.5 | 18.8 | 15.8 | 21.0 | 23.7 | 19.2 | 18.0 |
| E | 1017.0 | 1011.6 | 936.4 | 851.5 | 1145.7 | 1160.5 | 1018.4 | 972.8 |

Signals obtained for compounds 5 and 6 remained in a desirable range over the course of the testing reported in Table 10.

Compound 5 (2.5 mM) in 0.1 M Tris, 125 mM NaCl, 2 M $MgCl_2$, pH 8.3 was tested again under after six freeze/thaw cycles and storage at 2–8° C., as well as after continuous storage at 45° C. LCx® testing was done using duplicates of Calibrators A and E and the vials containing the compound 5 were also visually inspected for precipitation. No precipitation was observed in the solution after storage and the results reported in Table 11 are averages of the replicates from the LCx® testing.

TABLE 11

| | Mean LCx ® Performance (c/s/s) | | | |
|---|---|---|---|---|
| Calibrator | 0 | 45° C. 20 days | 45° C. 38 days | 45° C. 9 wks |
| A | 16.4 | 20.2 | 23.2 | 18.2 |
| E | 842.7 | 955.5 | 913.1 | 735.2 |

Table 11 indicates that after 9 weeks at 45° C. a decrease in signal of approximately 12% was obtained for both conditions. In other experiments, very little decrease in signal was obtained using a different lot of AUG stored at 45° C. for 9 weeks. These results indicate that compound 5 is very stable even when stored for long periods at elevated temperatures.

C. Performance in HIV-1 LCx® Assay Compound 5 and Compound 6 were used separately as substrates in assays to detect an internal control amplification product in an assay designed to detect HIV-1 RNA on the Abbott LCx® system. In this assay, a pair of primers (designated SEQ. ID. NO. 2 and SEQ. ID. NO. 3) were designed to amplify both an HIV target sequence (designated SEQ. ID. NO. 4) and an internal control sequence (designated SEQ. ID. NO. 5). To facilitate capture of amplification products, the reverse primer (SEQ. ID. NO. 2) was labeled with carbazole at the 5' end according to standard phosphoramidite methods described in U.S. Pat. No. 5,424,414. The forward primer (SEQ. ID. NO. 3) was not labeled.

Amplified internal control and HIV sequences were detected according to oligonucleotide hybridization as disclosed in U.S. patent application Ser. No. 08/514,704 (filed Aug. 14, 1995). SEQ. ID. NO. 6 was used as an internal hybridization probe designed to distinguish and detect the amplified internal control sequence. To facilitate detection with a conjugate, the 5' end of SEQ. ID. NO. 6 was labeled with two dansyl molecules using standard phosphoramidite methods mentioned above. SEQ. ID. NO. 7 was used as an internal hybridization probe designed to distinguish and detect the amplified HIV target sequence. To facilitate detection with a conjugate, the 5' end of SEQ. ID. NO. 7 was labeled with two adamantane molecules using the standard phosphoramidite methods mentioned above. Both probes were blocked at the 3' end with a phosphate group to avoid extension during the amplification reaction.

HIV-1 RNA was isolated from gradient purified virions (HIV-1, Advanced Biotechnologies Inc., Columbia, Md.) using the Qiagen RNA extraction procedure and column methodology as described by the manufacturer (Qiagen, Frankfurt, Germany). The viral RNA was quantitated in viral RNA copies per milliliter, and serially diluted into 2 ng-/l ribosomal RNA (Boehringer-Mannheim) in ten-fold dilutions containing $10^6$ to $10^1$ viral copies/25 ill.

Each of the dilutions of purified HIV-1 RNA (25 $\mu$l) were spiked with $1\times10^4$ molecules of the internal control sequence (in 25 $\mu$l), and both sequences (HIV-1 RNA and internal control) were reverse transcribed, PCR amplified and detected using the HIV-1 primers and probes described above. RT-PCR was performed using 50 mM Bicine, pH 8.25, 81.7 mM potassium acetate, 33.3 mM KOH, 0.1 mM EDTA, 8% glycerol, 0.01 mg/ml bovine serum albumin (BSA) and 0.02% sodium azide. Recombinant *Thermus thermophilus* polymerase was used at a concentration of 5 units/reaction, with dNTPs (dATP, dGTP, dTTP and dCTP) present at a final concentration of 0.15 mM each. Hence, the 10-fold dilutions of HIV-1 RNA extracted from virions were used as samples and 2 ng/$\mu$l ribosomal RNA was used as negative control. Samples and negative control were run in triplicate.

Reaction mixtures were reverse transcribed and amplified in a Perkin-Elmer 480 Thermal Cycler. Reaction mixtures were first incubated at 62° C. for 30 minutes to reverse transcribe the RNA, followed by 2 minutes at 94° C. PCR amplification was then initiated through a "touchdown" or "step-down" protocol to provide stringent conditions in the early stages of amplification. This utilized 8 cycles as follows: 1 cycle at 70° C. for 80 seconds then 94° C. for 30 seconds, followed by 1 cycle at 69° C. for 80 seconds then 94° C. for 30 seconds, followed by 1 cycle at 68° C. for 80 seconds then 94° C. for 30 seconds, followed by I cycle at 67° C. for 80 seconds then 94° C. for 30 seconds, followed by 1 cycle at 66° C. for 80 seconds then 94° C. for 30 seconds, followed by 1 cycle at 65° C. for 80 seconds then 94° C. for 30 seconds, followed by 1 cycle at 64° C. for 80 seconds then 94° C. for 30 seconds, followed by 1 cycle at 63° C. for 80 seconds then 94° C. for 30 seconds. Further amplification was then accomplished with 35 cycles at 62° C. for 80 seconds then 94° C. for 30 seconds. After the reaction mixtures were thermal cycled, the mixtures were maintained at 97° C. for 5 minutes and the HIV-1 specific and internal control specific probe hybridization was accomplished by lowering the temperature to 15° C. for 5 minutes. The reaction products were held at 4° C. until they were detected.

The reaction products were detected on the Abbott LCx® system. A suspension of anti-carbazole antibody coated microparticles (employed to capture the hybrid products from above), and an anti-adamantane antibody/alkaline phosphatase conjugate or an anti-dansyl antibody/beta-galactosidase conjugate (employed to detect the hybrid products from above) were used in conjunction with the LCx® to capture and detect the reaction products. All of these reagents are available from Abbott Laboratories, Abbott Park, Ill. Methyl-umbelliferyl phosphate (MUP, also available from Abbott Laboratories, Abbott Park, Ill.) was employed as the substrate for the alkaline phosphatase conjugate, and either (i) MUG at 0.6 mM in 0.1 M Tris, pH 8.3 containing 0.0005% sarafloxacin hydrochloride (a quinolone antimicrobial described above) and 0.01% Gentamycin Sulfate, or (ii) compound 5 or compound 6, both at 2.5 mM in separate solutions of 0.1 M Tris, 125 mM NaCl, 2 mM $MgCl_2$, pH 8.3 were used as the beta-galactosidase enzyme conjugate substrate. The rate of conversion of substrate to product was measured and reported as counts/second/second (c/s/s). The results are shown in Table 12 below.

TABLE 12

| HIV copies | Mean LCx ® Rate (c/s/s) | | | |
|---|---|---|---|---|
| | MUG | Compound 5 | Compound 6 | MUP* |
| 0 | 1431.2 | 2583.9 | 2883.4 | 277.0 |
| $10^1$ | 1322.1 | 2611.4 | 2900.7 | 600.1 |
| $10^2$ | 1303.3 | 2529.2 | 2755.4 | 1381.8 |
| $10^3$ | 1130.6 | 2282.3 | 2512.4 | 2089.2 |
| $10^4$ | 863.9 | 1794.1 | 1903.8 | 2441.0 |
| $10^5$ | 351.5 | 729.8 | 808.1 | 2695.4 |
| $10^6$ | 80.1 | 163.0 | 176.6 | 2855.4 |

(*average of 3 experiments)

As expected, the results in Table 12 demonstrate that the internal control reaction product, detected by an antibody conjugated with the enzyme beta-galactosidase and compound 5 or 6, decreased in inverse proportion to the amount of HIV sample RNA. This was expected because the HIV-1 RNA and internal control RNA competed for the primer sequences and the internal control RNA concentration remained constant at $1 \times 10^4$ molecules per reaction while the HIV-1 RNA was increased.

All 3 β-galactosidase substrates (used to detect the internal control product) produced a sufficiently detectable signal. However, compounds 5 and 6 gave higher signals and had a larger dynamic range than MUG. While the concentrations of compounds 5 and 6 were higher than the MUG concentration, higher concentrations of MUG were not used because MUG was shown to precipitate under certain conditions at higher concentrations.

While the invention has been described in detail and with reference to specific embodiments, it will be apparent to one skilled in the art that various changes and modifications may be made to such embodiments without departing from the spirit and scope of the invention.

What is claimed is:

1. A fluorescent enzyme substrate having the structure (I),

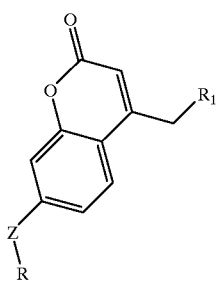

(I)

where R is an enzyme cleavable group; Z is O, S or Se; and $R^1$ is an amide.

2. The substrate of claim 1 where R is a monosaccharide, $-CO(CH_2)_aCH_3$, or $-PX(OR^2)_2$, where $R^2$ is hydrogen or lower alkyl, X is O or S, and a is 1 to 18.

3. The substrate of claim 2 wherein the galactose is β-D-monosaccharide.

4. The substrate of claim 1 wherein $R_1$ is a chain of atoms attached to said substrate (I) with an amide linkage wherein
   a) said chain of atoms attached to said compound (I) through said amide linkage is a branched or unbranched chain of 2–25 carbon atoms that terminates with a chemical group selected from the group consisting of $-OH$, $-NH_2$, $-OC_1-C_2$ alkyl, $-COOH$, $-N(C_1-C_2$ alkyl$)_2$, $-SO_3$, a heterocycle of 5–6 atoms that contains at least one N atom, and $-N(C_1-C_5$ alkyl amine$)_2$, and
   b) said branched or unbranched chain of 2–25 carbon atoms is optionally substituted with one or more heteroatoms.

5. The substrate of claim 4 wherein $R_1$ is $COR^3$, wherein $R^3$ is NHY, and Y is $-(CH_2)_1R^5$ wherein $R^5$ is $-CH_2OH$; $-COOH$;
$-OCH_3$; $-OH$, $-[O(CH_2)_m]_nCH_2OH$; $-[O(CH_2)_m]_n\ OCH_3$;
$-C[(CH_2)_mOH]_3$; a heterocycle of 5 or 6 atoms that contains at least one N atom; $-SO_3$; $-NH_2$; $-N[(CH_2)_mCH_3]_3$; or Y is
$-CH(R_6)(R_7)$; $-(CHOHCONH)_mCHOHCOOH$;
$-(CH2CONH)_mCH2COOH$ where $R_6$ is $-CH_2OH$ or $-COOH$ and $R_7$ is $-CH_2OH$ or $-(CH_2)_pNH_2$ and where 1, m, n, and p are independently 1 to 6.

6. The substrate of claim 5 wherein 1 is 1–3, m is 2 or 3, n is 2–3, p is 1 to 6 and q is 2–4.

7. The substrate of claim 5 wherein $R^3$ is NHY, and Y is selected from the group consisting of: $-(CH_2)_2OH$, $-C(CH_2OH)_3$, $-(CH_2)_2NH(CH_2)_2NH_2$, $-(CH_2)_2N[(CH_2)_2NH_2]_2$, $-[(CH_2)_2O]_2(CH_2)_2OCH_3$, $-(CH_2)_2OCH_3$, $-(CH_2)_2SO^-_3$, $-(CH_2)_2COOH$, and $-(CH_2)_2N^+(CH_3)_3$.

8. The substrate of claim 1 wherein and $R^1$ is selected from the group consisting of: $-CONH(CH_2)_2OH$, $-CONHC(CH_2OH)_3$, $-CONH(CH_2)_2NH(CH_2)_2NH_2$, $-CONH(CH_2)_2N[(CH_2)_2NH_2]_2$, $-CONH[(CH_2)_2O]_2(CH_2)_2OCH_3$, $-CONH(CH_2)_2OCH_3$, $-CONH(CH_2)_2SO^-_3$, $-CONH(CH_2)_2COOH$, and $-CONH(CH_2)_2N^+(CH_3)_3$.

9. A kit comprising at least one container containing the substrate of claim 1.

10. A fluorescent compound having the formula (II), below

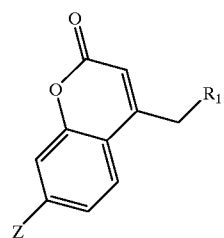

(II)

wherein Z is O, S or Se; and $R^1$ is an amide.

11. The compound of claim 10 wherein Z is O and $R^1$ is selected from the group consisting of: $-CONH(CH_2)_2OH$, $-CONHC(CH_2OH)_3$, $-CONH(CH_2)_2NH(CH_2)_2NH_2$, $-CONH(CH_2)_2N[(CH_2)_2NH_2]_2$, $-CONH[(CH_2)_2O]_2(CH_2)_2OCH_3$, $-CONH(CH_2)_2OCH_3$, $-CONH(CH_2)_2SO^-_3$, $-CONH(CH_2)_2COOH$, and $-CONH(CH_2)_2N^+(CH_3)_3$.

* * * * *